US009359632B2

(12) United States Patent
Loo et al.

(10) Patent No.: US 9,359,632 B2
(45) Date of Patent: Jun. 7, 2016

(54) DEVICES, SYSTEMS AND METHODS FOR SAMPLE PREPARATION

(71) Applicant: Theranos, Inc., Palo Alto, CA (US)

(72) Inventors: Alexander Loo, Palo Alto, CA (US); Elizabeth A. Holmes, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 0 days.

(21) Appl. No.: 14/203,436

(22) Filed: Mar. 10, 2014

(65) Prior Publication Data
US 2014/0272938 A1   Sep. 18, 2014

Related U.S. Application Data

(60) Provisional application No. 61/799,533, filed on Mar. 15, 2013.

(51) Int. Cl.
| | |
|---|---|
| *B06B 3/00* | (2006.01) |
| *C12Q 1/04* | (2006.01) |
| *B01F 11/02* | (2006.01) |
| C12N 1/06 | (2006.01) |
| G01N 35/00 | (2006.01) |

(52) U.S. Cl.
CPC .............. *C12Q 1/04* (2013.01); *B01F 11/0266* (2013.01); *B01F 11/0283* (2013.01); *B01L 2300/0609* (2013.01); *B01L 2400/0439* (2013.01); *C12N 1/066* (2013.01); *G01N 2035/00554* (2013.01); *G01N 2333/24* (2013.01); *G01N 2333/31* (2013.01)

(58) Field of Classification Search
None
See application file for complete search history.

(56) References Cited

U.S. PATENT DOCUMENTS

| | | | | |
|---|---|---|---|---|
| 5,876,671 | A * | 3/1999 | Beugelsdijk | G01N 33/24 422/128 |
| 6,598,466 | B1 * | 7/2003 | Deluca | G01N 15/0227 73/150 A |
| 8,088,593 | B2 | 1/2012 | Burd et al. | |

(Continued)

FOREIGN PATENT DOCUMENTS

| | | |
|---|---|---|
| EP | 0337690 A1 | 10/1989 |
| WO | 2011156432 A2 | 12/2011 |
| WO | 2013052318 A1 | 4/2013 |

OTHER PUBLICATIONS

International Search Report and Written Opinion dated Aug. 14, 2014 for Application No. PCT/US2014/022847.

*Primary Examiner* — Erik B Crawford

(57) ABSTRACT

Devices, systems and methods including a sonicator for sample preparation are provided. A sonicator may be used to mix, resuspend, aerosolize, disperse, disintegrate, or de-gas a solution. A sonicator may be used to disrupt a cell, such as a pathogen cell in a sample. Sample preparation may include exposing pathogen-identifying material by sonication to detect, identify, or measure pathogens. A sonicator may transfer ultrasonic energy to the sample solution by contacting its tip to an exterior wall of a vessel containing the sample. Multipurpose devices including a sonicator also include further components for additional actions and assays. Devices, and systems comprising such devices, may communicate with a laboratory or other devices in a system for sample assay and analysis. Methods utilizing such devices and systems are provided. The improved sample preparation devices, systems and methods are useful for analyzing samples, e.g. for diagnosing patients suffering from infection by pathogens.

13 Claims, 9 Drawing Sheets

Solenoid Off

(56) References Cited

U.S. PATENT DOCUMENTS

| | | | |
|---|---|---|---|
| 8,380,541 B1 | 2/2013 | Holmes | |
| 8,435,738 B2 | 5/2013 | Holmes | |
| 2006/0027686 A1* | 2/2006 | Taylor et al. | 241/2 |
| 2006/0121603 A1* | 6/2006 | Yuan | C12M 47/06 435/306.1 |
| 2011/0318728 A1 | 12/2011 | Phan et al. | |
| 2013/0078624 A1 | 3/2013 | Holmes et al. | |
| 2014/0057255 A1 | 2/2014 | Holmes | |
| 2014/0057770 A1 | 2/2014 | Holmes et al. | |
| 2014/0073043 A1 | 3/2014 | Holmes | |

\* cited by examiner

Solenoid Off

Solenoid On

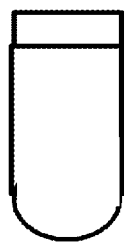
11A
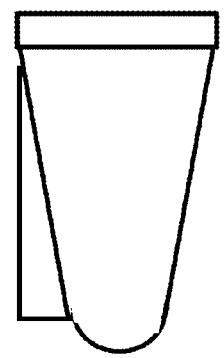
11B
11C
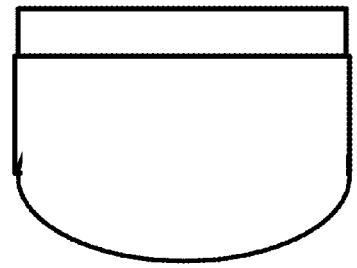
11D

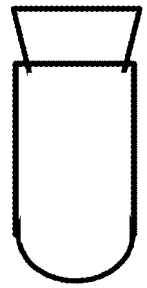
12A
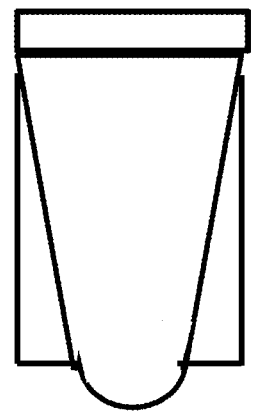
12B
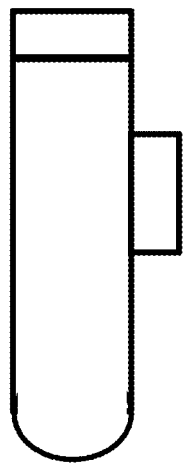
12C
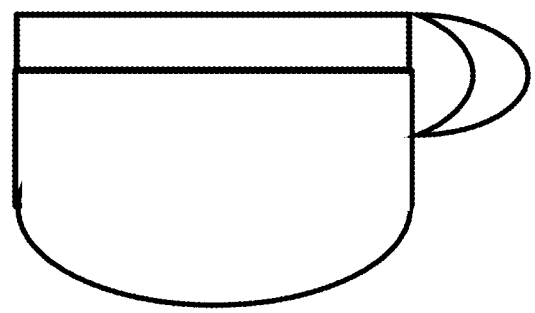
12D

DEVICES, SYSTEMS AND METHODS FOR SAMPLE PREPARATION

CROSS-REFERENCE TO RELATED APPLICATION

This application claims priority under 35 U.S.C. §119(e) to U.S. Patent Application Ser. No. 61/799,533, filed Mar. 15, 2013.

BACKGROUND

Rapid and accurate detection and identification of pathogens such as bacteria is important, and can be critical, in the diagnosis and treatment of infectious diseases, and in the prevention or amelioration of pandemics or epidemics. However, methods for detecting or identifying pathogens often require large samples, which can be difficult to obtain, or may be uncomfortable or painful for the subject. Methods for detecting or identifying pathogens often require the incubation of samples on growth media, or in host cells or animals, and so take long periods of time. Many pathogens are difficult to culture, or are similar to other organisms, and so are difficult to identify even if the sample yields a detectable culture. In addition, methods for detecting or identifying pathogens may require rare or expensive reagents or culture conditions.

Thus, detection and identification of pathogens in a biological sample may be important in the diagnosis and treatment of patients exposed to, or suspected of suffering, from infectious diseases. However, present methods for detecting or identifying pathogens are often inaccurate, difficult, expensive, and time-consuming. Accordingly, rapid, accurate and straightforward methods for the detection and identification of pathogens from small samples are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Devices, systems and methods for sample preparation are disclosed. Devices for sample preparation as disclosed herein comprise a sonicator; the sonicator may be configured to provide ultrasonic energy to a sample solution. A sample solution may be contained within a vessel. In embodiments, a sonicator may be used to mix a solution, e.g., to mix a sample solution, or to mix two or more solutions, such as a sample solution and a reagent solution. In embodiments, a sonicator may be used for emulsification of a solution or a mixture of solutions, or of a sample in a solution or reagent. In embodiments, a sonicator may be used for resuspension of a material, e.g., resuspension of a sample following centrifugation of the sample. In embodiments, a sonicator may be used for aerosolization of a liquid, e.g., aerosolization of a liquid sample, or of a solution comprising a sample. In embodiments, a sonicator may be used to heat a solution, such as a sample, or a solution comprising a sample. In embodiments, a sonicator may be used for dispersing a sample, or a sample in a solution, or other material, such as, e.g., dispersing a solid or semi-solid sample in a solution. In embodiments, a sonicator may be used to disintegrate a material, such as a sample, e.g., a solid or semi-solid sample may be exposed to sonication for disintegration, which may aid in its subsequent mixing into a reagent such as a diluent. In embodiments, a sonicator may be used to de-gas a liquid, such as a fluid sample; in embodiments, gas released in this way may become better available for assay. In embodiments, a sonicator may be used to disrupt a cell, such as a pathogen cell in a sample.

Pathogens may be detected and identified by their characteristic genetic material and characteristic proteins. Detection and identification of pathogens in a biological sample typically requires disruption of the pathogen to expose its nuclear material to testing, and to provide more accessible proteins and protein/membrane complexes for assay. Pathogen-identifying material may be released from the pathogen by disruption, e.g., by disruption of a pathogen membrane or cell wall. For example, disruption of the plasma membrane of any cell, or of a nuclear membrane of a eukaryotic pathogen, or disruption of the cell wall of a bacterium having a cell wall, or a combination of the same, may be effective to free pathogen-identifying material (e.g., DNA, RNA, or protein) for contact with assay reagents for detection, identification, or measurement.

Devices, systems and methods for disrupting pathogens in a biological sample are provided. Devices, systems and methods for disrupting pathogens in a biological sample as disclosed herein comprise a sonicator; the sonicator may be configured to provide ultrasonic energy to a sample solution containing a pathogen effective to disrupt the pathogen, e.g., to disrupt a membrane of the pathogen. Such disruption may be effective to release pathogen-identifying material from the pathogen, aiding in the detection, identification, or measurement of the pathogen. In embodiments, multipurpose devices are provided which include a sonicator configured to disrupt pathogen cells in a biological sample, exposing pathogen-identifying material for assay. Multipurpose devices are provided which include a sonicator configured to disrupt pathogen cells in a biological sample, exposing pathogen-identifying material for assay, and which may also perform at least one additional assay are provided. Systems comprising such devices are provided. Systems comprising such devices may further communicate with a laboratory or with other devices in a system for the detection and identification of pathogens, and for diagnosis of infectious diseases. Methods utilizing such devices and systems are provided. The devices, systems and methods disclosed herein provide advantages useful for diagnosing and treating patients suspected of, or suffering from, infection by pathogens. A biological sample may comprise blood, urine, sputum, tears, material obtained from a nasal swab, throat swab, cheek swab, or other sample obtained from a subject.

Applicants disclose devices configured to assay a biological sample for the presence of pathogen-identifying material, said devices comprising a sonicator, said sonicator being configured to contact a vessel containing said biological sample. Such a sonicator may be configured for use in the performance of said assay. A sonicator in a device as disclosed herein may be configured to contact a wall of a vessel containing at least a portion of a biological sample, effective to provide ultrasonic energy to said wall, effective to disrupt a pathogen in said biological sample and to release pathogen-identifying material from said pathogen. An assay may comprise detection of pathogen-identifying material; an assay may comprise identification of pathogen-identifying material; an assay may comprise measuring pathogen-identifying material, e.g., measuring an amount of pathogen-identifying material in a sample or portion of a sample. Such pathogen-identifying material may be detected, or may be identified, or may be measured, in an assay performed with said biological sample. In embodiments, a device disclosed herein may be configured to perform one or more other assay in addition to an assay directed to the detection, identification, or measurement of pathogen-identifying material.

A device as disclosed herein may be suitable for detection, identification, or measurement of pathogen-identifying material in a biological sample. In embodiments, a device for assaying a sample for the presence of pathogen-identifying material in a sample may comprise a sonicator, wherein said sonicator comprises means for contacting a wall of a vessel containing at least a portion of a biological sample. In embodiments, a device for assaying a sample for the presence of pathogen-identifying material in a sample may comprise: a sonicator; an sample handling system for transporting at least a portion of a biological sample; a vessel holder effective to hold a vessel having a wall; and a detector effective to detect or measure pathogen-identifying material (e.g., an optical detector). In embodiments, a sonicator may comprise a tip; in embodiments, a sonicator tip may be effective to contact said vessel wall and to transfer ultrasonic energy to said vessel wall from said sonicator. In embodiments, a sonicator may comprise a sonicator horn, which horn may have a tip, and said horn and tip may be effective to contact said vessel wall and to transfer ultrasonic energy to said vessel wall from said sonicator. In embodiments, a device may further comprise a communication assembly, which may comprise a display element or a communication element effective to report the results of said detection and/or measurement. In embodiments, a communication assembly, such as a display element and/or communication element, may be suitable for two-way communication.

In embodiments, a device for assaying a sample for the presence of pathogen-identifying material in a sample may comprise a sonicator, wherein said sonicator comprises means for contacting a wall of a vessel containing at least a portion of a biological sample. In embodiments, a device for assaying a sample for the presence of pathogen-identifying material in a sample may comprise: a sonicator; sample handling system means for transporting at least a portion of a biological sample; means for holding a vessel having a wall; means for contacting said vessel wall with at least a portion of said sonicator; and means for detecting, identifying, or measuring pathogen-identifying material (e.g., means for detecting an optical signal, and/or measuring an optical property of the combined composition with sample). In embodiments, a device may further comprise means for displaying or reporting the results of said detection and/or measurement. In embodiments, a sonicator may comprise a tip means, which may comprise a sonicator horn, configured to make effective contact with a surface, such as a vessel wall, effective to transfer ultrasonic energy from said sonicator to said surface. In further embodiments, a device for assaying a sample for the presence of pathogen-identifying material in a sample may comprise one or more of: detection means (e.g., an optical detector) for detecting the target; display means; and communication means for reporting the results of said detection and/or measurement. In embodiments, display means and/or communication means may be suitable for two-way communication.

Applicants further disclose systems comprising a device as disclosed herein. In embodiments, a system as disclosed herein may be used to detect the presence of, identify, or measure the amount of, pathogen-identifying material in a sample.

Applicants disclose herein systems for detecting the presence of pathogen-identifying material in a biological sample, e.g., a sample of blood, urine, sputum, tears, material from a nasal swab, throat swab, cheek swab, or other sample obtained from a subject. In embodiments, a system for detecting the presence of pathogen-identifying material in a sample may comprise a device as disclosed herein, and a means for communicating information from said device to a computer, a computer network, a telephone, a telephone network, or a device configured to display information communicated from said device.

Applicants disclose herein systems for identifying pathogen-identifying material in a biological sample, e.g., a sample of blood, urine, sputum, tears, material from a nasal swab, throat swab, cheek swab, or other sample obtained from a subject. In embodiments, a system for identifying pathogen-identifying material in a sample may comprise a device as disclosed herein, and a means for communicating information from said device to a computer, a computer network, a telephone, a telephone network, or a device configured to display information communicated from said device.

Applicants disclose herein systems for measuring the amount of pathogen-identifying material in a biological sample, e.g. a sample of blood, urine, sputum, tears, material from a nasal swab, throat swab, cheek swab, or other sample obtained from a subject. In embodiments, a system for measuring the amount of pathogen-identifying material in a sample may comprise a device as disclosed herein, and a means for communicating information from said device to a computer, a computer network, a telephone, a telephone network, or a device configured to display information communicated from said device.

It will be understood that a means for communicating information may include means for one-way communication and may include means for two-way communication, and may include means for communication with multiple locations or entities. In embodiments, a system for detecting the presence of pathogen-identifying material in a sample, a system for identifying pathogen-identifying material in a sample, and a system for measuring the amount of pathogen-identifying material in a sample, may comprise a device as disclosed herein, and a communication assembly, which may comprise a channel for communicating information from said device to a computer, said wherein said channel is selected from a computer network, a telephone network, a metal communication link, an optical communication link, and a wireless communication link. It will be understood that a communication assembly, e.g., comprising a channel for communicating information, may comprise a one-way communication channel and may be a two-way communication channel, and may comprise channels for communication with multiple locations or entities.

The methods disclosed herein may be performed on a device, or on a system, for processing a sample as disclosed herein. The methods disclosed herein can be readily incorporated into and used in an automated assay device, and in an automated assay system, as disclosed herein. For example, systems as disclosed herein may include a communication assembly for transmitting or receiving a protocol based on the analyte to be detected (e.g., pathogen-identifying material) or based on other analytes to be detected by the device or system. In embodiments, an assay protocol may be changed based on optimal scheduling of a plurality of assays to be performed by a device, or may be changed based on results previously obtained from a sample from a subject, or based on results previously obtained from a different sample from the subject. In embodiments, a communication assembly may comprise a channel for communicating information from said device to a computer, said wherein said channel is selected from a computer network, a telephone network, a metal communication link, an optical communication link, and a wireless communication link. In embodiments, systems as disclosed herein may transmit signals to a central location, or to an end user, and may include a communication assembly for transmitting such signals. Systems as disclosed herein may be configured for updating a protocol as needed or on a regular basis.

Accordingly, Applicants disclose devices configured to detect, identify, or measure pathogen-identifying material in a biological sample, e.g., of blood, urine, sputum, material obtained from a nasal swab, a throat swab, a cheek swab, or other sample. Such detection, identification, or measurements may be made according to a method disclosed herein. Devices configured to detect, identify, or measure pathogen-identifying material in a biological sample, e.g., of blood, urine, sputum, material obtained from a nasal swab, a throat swab, a cheek swab, or other sample, according to a method disclosed herein may be configured to determine pathogen-identifying material from a biological sample that comprises no more than about 1000 µL of a biological sample, or no more than about 500 µL of a biological sample, or no more than about 250 µL of a biological sample, or no more than about 150 µL of a biological sample, or no more than about 100 µL of a biological sample, or no more than about 50 µL of a biological sample, or, in embodiments, wherein said sample of blood comprises no more than about 25 µL of a biological sample, or wherein said sample of blood comprises no more than about 10 µL of a biological sample, or wherein said sample of blood comprises less than about 10 µL of a biological sample. Such devices may be configured to detect, identify, or measure pathogen-identifying material in a biological sample, e.g., of blood, urine, sputum, material obtained from a nasal swab, a throat swab, a cheek swab, or other sample, in less than about one hour, or, in embodiments, in less than about 40 minutes, or in less than about 30 minutes, or in less than about 20 minutes, or less than about 10 minutes, or less than about 5 minutes, or less.

Devices disclosed herein may be configured to perform an assay for the detection, identification, or measurement of pathogen-identifying material, and also to perform an assay for the measurement of another analyte in the biological sample, e.g., of blood, urine, sputum, material obtained from a nasal swab, a throat swab, a cheek swab, or other sample. Devices disclosed herein may be configured to perform an assay for the detection, identification, or measurement of pathogen-identifying material, and also to perform an assay comprising measurement of a morphological characteristic of a blood cell in the biological sample, e.g., of blood, urine, sputum, material obtained from a nasal swab, a throat swab, a cheek swab, or other sample. Devices disclosed herein may be configured to perform an assay for the detection, identification, or measurement of pathogen-identifying material, and also to perform an assay comprising measurement of another analyte, e.g., a vitamin, a hormone, a drug or metabolite of a drug, or other analyte. Such devices may be configured wherein the assays, or the order of performance of assays, that are performed by said device may be altered by communication with another device.

Applicants also disclose systems comprising a device as disclosed herein. In embodiments, the system comprises a device that is configured to perform an assay for the measurement of pathogen-identifying material and also to perform an assay for the measurement of another analyte in the biological sample, e.g., of blood, urine, sputum, material obtained from a nasal swab, a throat swab, a cheek swab, or other sample. In embodiments, the system comprises a device that is configured to perform an assay for the measurement of pathogen-identifying material and also to perform an assay for the measurement of a morphological characteristic of a blood cell in the biological sample, e.g., of blood, urine, sputum, material obtained from a nasal swab, a throat swab, a cheek swab, or other sample. In embodiments of such a system, assays, or the order of performance of assays, that are performed by said device may be altered by communication with another device.

Applicants disclose herein a method of disrupting a pathogen in a biological sample, comprising: transporting at least a portion of a biological sample to a vessel, said vessel having an interior portion and an exterior wall, effective to place said portion of said biological sample into said interior portion of said vessel; contacting an exterior wall of said vessel containing said biological sample with a sonicator; and applying ultrasound energy to said wall of the vessel effective to disrupt a target pathogen in said biological sample. In embodiments, such transporting of at least a portion of a biological sample to a vessel may comprise transporting by sample handling system.

Applicants disclose herein a method of detecting the presence of pathogen-identifying material in a biological sample, comprising: transporting at least a portion of a biological sample to a vessel, said vessel having an interior portion and an exterior wall, effective to place said portion of said biological sample into said interior portion of said vessel; contacting an exterior wall of said vessel containing said biological sample with a sonicator; applying ultrasound energy to said wall of the vessel effective to release pathogen-identifying material from a target pathogen in said biological sample; and detecting the presence of pathogen-identifying material. In embodiments, such transporting of at least a portion of a biological sample to a vessel may comprise transporting at least a portion of a biological sample by a sample handling system.

Applicants disclose herein a method of identifying a pathogen in a biological sample, comprising: transporting at least a portion of a biological sample to a vessel, said vessel having an interior portion and an exterior wall, effective to place said portion of said biological sample into said interior portion of said vessel; contacting an exterior wall of said vessel containing said biological sample with a sonicator; applying ultrasound energy to said wall of the vessel effective to disrupt a target pathogen in said biological sample; and identifying a pathogen in the sample. In embodiments, such transporting of at least a portion of a biological sample to a vessel may comprise transporting at least a portion of a biological sample by a sample handling system.

Applicants disclose herein a method of measuring the amount of pathogen-identifying material in a biological sample, comprising: transporting at least a portion of a biological sample to a vessel, said vessel having an interior portion and an exterior wall, effective to place said portion of said biological sample into said interior portion of said vessel; contacting an exterior wall of said vessel containing said biological sample with a sonicator; applying ultrasound energy to said wall of the vessel effective to release pathogen-identifying material from a target pathogen in said biological sample; and measuring the amount of pathogen-identifying material. In embodiments, such transporting of at least a portion of a biological sample to a vessel may comprise transporting at least a portion of a biological sample by a sample handling system.

Applicants disclose herein devices and systems comprising a sonicator, and methods using such device and systems to detect, identify, or measure pathogens in a sample by detecting, identifying, or measuring pathogen-identifying material released in a sample as a result of disruption caused by application of ultrasonic energy to the sample. As disclosed herein, ultrasonic energy may be applied to a sample by direct contact between the sample and a sonicator (e.g., between a sample and a tip portion of a sonicator); by indirect contact between a sample and a sonicator, wherein the sonicator contacts a compliant barrier that is in contact with a sample; by indirect contact between a sample and a sonicator, wherein the sonicator contacts a wall of a vessel containing a sample; or by other means. Ultrasonic energy suitable for disrupting pathogens using devices, systems, and methods as disclosed herein includes ultrasonic energy between about 20 kiloHertz (kHz) and about 60 kHz; between about 20 kHz and about 50 kHz; between about 20 kHz and about 40 kHz; or between about 20 kHz and about 30 kHz. Ultrasonic energy suitable for disrupting pathogens using devise, systems, and methods as disclosed herein includes ultrasonic energy at or about 20 kHz; at or about 25 kHz; at or about 28 kHz; at or about 30 kHz; at or about 35 kHz; at or about 40 kHz; at or about 45 kHz; at or about 50 kHz; at or about 55 kHz; or at or about 60 kHz.

In embodiments, pathogen-identifying material may comprise a nucleic acid, and may comprise a pathogen-identifying sequence of nucleic acids. In embodiments, pathogen-identifying material may comprise an amino acid, and may comprise a pathogen-identifying sequence of amino acids. In embodiments, detecting the presence of pathogen-identifying material comprises contacting said pathogen-identifying material with a probe, which may be a labeled probe. In embodiments, a probe, including a labeled probe, may comprise nucleic acids. In embodiments, a probe, including a labeled probe, may comprise a sequence of nucleic acids complementary to at least a portion of said pathogen identifying material. In embodiments, a probe, including a labeled probe, may comprise amino acids. In embodiments, a probe, including a labeled probe, may comprise an antibody or an antibody fragment which specifically binds to at least a portion of said pathogen-identifying material.

In embodiments, a probe, or a complex, may comprise a label. In embodiments, a label may be selected from the group consisting of a dye, an epitope tag, a fluorescent moiety, a luminescent moiety, a chemiluminescent moiety, an enzymatic label, a magnetic label, a paramagnetic label, a contrast agent, a nanoparticle, a radioisotope, biotin, streptavidin, and a quencher.

In embodiments, detecting the presence of pathogen-identifying material may comprise detecting a complex comprising pathogen-identifying material, or detecting a probe bound to pathogen-identifying material in said sample. In embodiments of the methods disclosed herein, a detecting step may comprise detecting the presence of a label.

In embodiments, identifying a pathogen-identifying material may comprise identifying a complex comprising pathogen-identifying material, or detecting a probe bound to pathogen-identifying material in said sample. In embodiments of the methods disclosed herein, an identifying step may comprise detecting the presence of a label.

In embodiments, measuring the amount of pathogen-identifying material may comprise measuring the amount of a complex comprising pathogen-identifying material, or measuring the amount of probe bound to pathogen-identifying material in said sample. In embodiments of the methods disclosed herein, a measuring step may comprise measuring the amount of probe, or label, bound or released, may comprise measuring a label or measuring the amount of a label.

In embodiments of the methods disclosed herein, detecting probe bound to pathogen-identifying material may comprise an optical measurement, identifying pathogen-identifying material may comprise an optical measurement, and measuring the amount of probe bound may comprise an optical measurement. In embodiments, optical measurement may comprise detection of, or measurement of, the intensity of electromagnetic radiation passing through, or emitted from, a composition comprising said biological sample.

Methods, devices, and systems disclosed herein provide rapid assays which require only small amounts of sample, such as only small amounts of blood. Device and systems disclosed herein are configured to perform such rapid assays which require only small amounts of sample, such as only small amounts of blood, urine, sputum, tears, material obtained from a nasal swab, throat swab, cheek swab, or other biological sample. Accordingly, the methods, devices, and systems provide rapid tests, which require only small biological samples, and thus provide advantages over other methods, compositions, assays, devices, and systems.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 6A shows a side view of an embodiment of a sonicator mounted with a solenoid configured to move the sonicator horn in a transverse direction (e.g., towards the vessel holder, or away from the vessel holder, as shown in the figure). A spring is provided to urge the sonicator away from the vessel holder upon release of solenoid force drawing the sonicator towards the vessel holder. The sonicator horn is disposed so as to approach a vessel held within the vessel holder. At rest (with the solenoid off), as shown in FIG. 6A, the sonicator horn does not contact a vessel held within the vessel holder, and the spring is in an extended conformation.

FIG. 6B shows a side view of an embodiment of a sonicator mounted with a solenoid configured to move the sonicator horn in a transverse direction (e.g., towards the vessel holder, or away from the vessel holder, as shown in the figure). A spring is provided to urge the sonicator away from the vessel holder upon release of solenoid force drawing the sonicator towards the vessel holder. The sonicator horn is disposed so as to approach a vessel held within the vessel holder. With the solenoid on, as shown in FIG. 6B, the sonicator horn is in contact with an outer wall of a vessel held within the vessel holder, and the spring is in a compressed conformation. Operation of the sonicator in this configuration, in which the sonicator horn is in contact with a wall of a vessel held within the vessel holder, is effective to provide ultrasonic energy to a sample solution within the vessel. Providing sufficient ultrasonic energy for s sufficient amount of time is effective to disrupt cells within the sample solution; in particular, pathogen cells within the sample solution may be disrupted, effective to release pathogen-identifying material for detection, identification, and measurement.

FIG. 10A shows a side view of a vessel, with a flat wall surface facing outward, and the opening (for filling the vessel) shown at the top. The bottom of the vessel shown is also flat; the flat side wall and the flat bottom are configured to contact a tip portion of a sonicator, such as a tip of a sonicator horn. The wider portion at the top of the vessel includes surfaces and mating sockets. The mating sockets comprise recesses configured for engagement of a transport and/or force-providing member (e.g., a nozzle of a sample handling system) which a) allows transport of the vessel and b) provides a surface for provision of downward force to oppose upward force of a sonicator horn placed on a flat bottom surface of the vessel. FIG. 10B shows a side view of a vessel as shown in FIG. 10A, with a flat wall surface facing rightward, and the opening (for filling the vessel) shown at the top. FIG. 10C shows a vessel as shown in FIGS. 10A and 10B, with a flat wall surface facing leftward and slightly upward, and the opening (for filling the vessel) shown at the top. Openings of the mating sockets are visible in this view, as is an inner ridge within the internal chamber of the vessel. An inner ridge as illustrated in the figure may be configured to seat, or to seal, a cap. FIG. 10D shows a cross-sectional view of a vessel as shown in FIGS. 10A-C, with the opening (for filling the vessel) shown at the top. The ridge and inner chamber of the vessel, and the shape and depth of the mating sockets are visible in this cross-sectional view.

FIGS. 11A-11D provide further embodiments of vessels suitable for containing a sample solution for sonication. FIG. 11A shows an embodiment of a tubular vessel with a rounded bottom. FIG. 11B shows an embodiment of a conical vessel with a rounded bottom. FIG. 11C an embodiment of an elongated tubular vessel with a rounded bottom. FIG. 11D shows an embodiment of a wide tubular vessel with a rounded bottom.

FIGS. 12A-12D provide yet further embodiments of vessels suitable for containing a sample solution for sonication. FIG. 12A shows an embodiment of a tubular vessel with a rounded bottom and a tapered (e.g., partially conical-shaped cap). FIG. 12B shows an embodiment of a conical vessel with a rounded bottom having flat side surfaces configured to engage with a sonicator tip. FIG. 12C an embodiment of an elongated tubular vessel with a rounded bottom and a protruding flat surface configured to engage with a sonicator tip. FIG. 12D shows an embodiment of a wide tubular vessel with a rounded bottom having a cap connected to the vessel via cap linkage.

DETAILED DESCRIPTION

Figure 1:
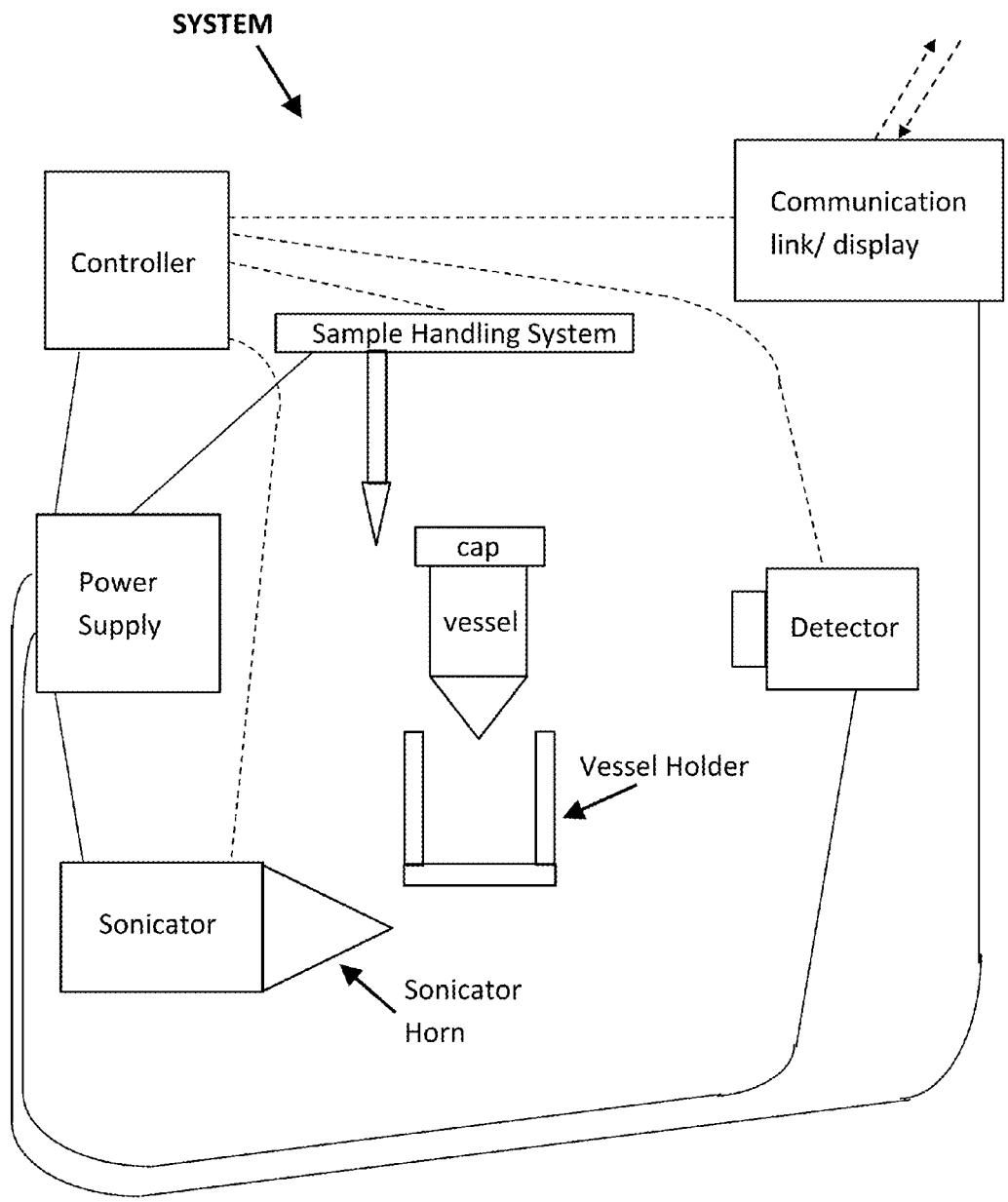
FIG. 1 presents a schematic illustration of an embodiment of a system as disclosed herein, including a sonicator having a sonicator horn, a vessel configured to hold a sample, a vessel holder configured to hold a vessel for sonication, a sample handling system configured to place a sample within a vessel, a detector for detecting pathogen-identifying material from a sample, a communications assembly (labeled communication link/display), which may comprise a display, for receiving instructions and information, and for providing information and data to a user, or to other components or equipment, a controller to operate the components of the system, and a power supply to enable the operation of the components.

Applicants provide devices, systems, and methods for disrupting cells using a sonicator. Sonicators provide ultrasonic energy which disrupts cells by producing, for example, cavitation within a sample fluid containing the cells, which cells may be disrupted by sonoporation due to cavitation in the fluid. In embodiments, such devices, systems, and methods for disrupting cells using a sonicator may be applied to an external surface of a vessel, where the vessel contains a biological sample suspected of harboring a pathogen or multiple pathogens. A sonicator may provide ultrasonic energy to a vessel, for example, by contacting a wall of the vessel with its tip portion (e.g., with a tip of a sonicator horn), effective to transfer energy through the vessel wall to fluid within the vessel. Such fluid may comprise a biological sample. Applicants further disclose vessels for use with sonicators as disclosed herein and with devices and systems comprising such sonicators.

Accordingly, embodiments of devices and systems for detecting, identifying, or measuring pathogen-identifying material in at least a portion of a biological sample, e.g., of blood, urine, sputum, material obtained from a nasal swab, a throat swab, a cheek swab, or other sample; and embodiments of devices and systems for detecting, identifying, or measuring pathogen-identifying material in at least a portion of a biological sample, e.g., of blood, urine, sputum, material obtained from a nasal swab, a throat swab, a cheek swab, or other sample, and at least one other biologically relevant attribute from said biological sample, e.g., of blood, urine, sputum, material obtained from a nasal swab, a throat swab, a cheek swab, or other sample, from a subject are disclosed herein.

Devices, systems, and methods disclosed herein may comprise, and may be used with, devices, systems, and methods as disclosed in, for example, U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

Devices disclosed herein comprise a sonicator configured to transfer ultrasonic energy to a sample solution. In embodiments, a sonicator, e.g., a sonicator tip, may contact a sample solution directly. In embodiments, a sonicator, e.g., a sonicator tip, may contact a sample solution indirectly via a barrier material. In embodiments, a barrier material may be a compliant material. In embodiments, a sonicator, e.g., a sonicator tip, may not contact a sample solution directly, but may instead be configured to contact a wall or other surface of a vessel containing a solution to which ultrasonic energy is to be directed.

A sonicator may comprise a sonicator horn, e.g., may comprise an elongated portion configured to transmit and/or concentrate ultrasonic energy at a small area distal from the oscillator of the sonicator. A sonicator (and its sonicator horn) may have a tip configured to contact and to interact with a vessel containing a solution to which ultrasonic energy is to be directed. In embodiments, a sonicator may be mounted on a sonicator mount, which may be configured to hold a sonicator in an operating position during use. In embodiments, a sonicator may be mounted on a sonicator mount, which may be configured to place a sonicator in a disengaged position when not in use transmitting ultrasonic energy.

In embodiments, a sonicator mount may provide for movement of the sonicator, e.g., may allow the engagement and disengagement of the sonicator with a vessel wall, as needed for the operation of the sonicator. For example, a device comprising a sonicator may include a sonicator mount operably connected with a solenoid configured to place a sonicator tip in contact with a vessel containing a sample solution when the solenoid is activated, where the sonicator is mounted effective that the sonicator tip is removed from contact with the vessel when the solenoid is not activated. In embodiments, a spring may be used to aid in removing a sonicator tip from contact with a vessel when a solenoid is not activated.

In embodiments, a sample solution may be contained in a vessel, and a portion of a sonicator may be applied to an external wall of the vessel. In embodiments, the external wall to which a sonicator is applied may be a side wall of the vessel. In embodiments, the external wall to which a sonicator is applied may be a bottom wall of the vessel. In embodiments, the external wall to which a sonicator may be applied is a top wall of the vessel. In embodiments, a sonicator may be applied to more than one wall of the vessel.

A vessel comprises an internal chamber configured for holding fluid, such as a sample solution (although it will be understood that such an internal chamber may hold a reagent, or water, or any other fluid). A vessel will typically include an opening configured to accept a sample solution; for example, a vessel may be filled (partially or completely) via an opening. Where the vessel has only a single opening leading to an inner chamber, that opening defines the top of the vessel. In embodiments, the vessel is open to the environment, e.g., has an open passage at its top. In embodiments, a vessel may be configured to accept a cap, where the cap is effective to occlude an opening in the vessel, e.g., to close an open passage at the top of the vessel. In embodiments, a cap may be a separate element (e.g., may be able to be completely separated from the vessel); in embodiments, a cap may be a portion of a vessel capable of moving into and out of a position that occludes an opening or passage that (when not occluded) provides access to an interior portion of the vessel. In embodiments, a cap may comprise a portion of a vessel. For example, a cap may be connected to other portions of a vessel by a hinge, or by a thread, or cable, or other flexible connector of any kind. In embodiments, the vessel is closed, and not open to the environment, when ultrasonic energy is applied to it. A cap, when in place occluding an opening of a vessel, may be effective to prevent or reduce spilling of a sample solution held within the vessel. A cap, when in place occluding an opening of a vessel, may be effective to prevent or reduce loss of sample solution due to splashing, bubble formation, aerosolization, or other actions due to delivery of ultrasonic energy to a sample solution held within the vessel.

In embodiments of the devices, systems and methods disclosed herein, a sample handling system may be used to transport and deliver a sample solution to a vessel, and to fill a vessel (either partially or fully) with a sample solution. In embodiments, a sample handling system comprises a pipette. A pipette may be configured to accept a pipette tip, e.g., to mount and transport a pipette tip attached to the pipette. In embodiments, a pipette comprises a nozzle configured to accept a pipette tip. A pipette may be configured to aspirate a fluid, such as a sample solution, into a pipette tip attached to the pipette (e.g., a pipette tip which is attached to a nozzle of the pipette). In embodiments, a pipette may be configured to dispense a fluid, such as a sample solution, from a pipette tip attached to the pipette (e.g., to a nozzle of the pipette). A pipette may be configured to transmit force to a surface or component of a device. In embodiments, a pipette nozzle may contact a surface or component of a device, effective to transmit force to that surface or component. In embodiments, a pipette nozzle may contact a mating recess of a vessel, and, in embodiments, may engage a mating recess of a vessel. In embodiments, two, or more pipette nozzles may contact mating recesses of a vessel, and, in embodiments, may engage mating recesses of a vessel. In embodiments, a pipette of a sample handling system may be movable, and is preferably movable in at least two, and more preferably in three dimensions (e.g., is movable in one, two, or all three of horizontally, laterally, and vertically).

In embodiments, devices comprising a sonicator, and systems and methods comprising or using such devices, may comprise a detector configured to detect pathogen-identifying material in a sample. A detector may be, for example, an optical detector, such as a spectrophotometer, a photomultiplier, a charge-coupled device, a camera, or other device or system configured to detect a light-based signal indicative of the presence of a pathogen-identifying material. In embodiments, a detector may be configured to, or be effective to, detect a signal comprising chemiluminescence, luminescence, fluorescence, absorbance, transmittance, turbidity, a color change, or other change in light, whether emitted, transmitted, or absorbed, effective to signal the presence of a pathogen-identifying material in a sample. In embodiments, a detector may comprise an electrochemical detector, or a temperature sensor, or a pH sensor, or a radiation sensor, or an ion-sensitive electrode, or other sensor capable of detecting the presence of a pathogen-identifying material in a sample.

Methods for detecting pathogen-identifying material include assays for detecting nucleic acids (e.g., DNA or RNA), assays for detecting peptides and proteins (including glycoproteins), assays for detecting other pathogen-related molecules, complement fixation assays, hemagglutination assays (e.g., for influenza), and other assays. Methods for detecting nucleic acids include polymerase chain reaction (PCR) methods (including quantitative PCR (qPCR), reverse-transcriptase PCD (RT-PCR), "real-time" PCR, one-step PCR, two-step PCR, and other methods known in the art. Methods for detecting peptides and proteins include enzyme immunoassays such as Enzyme-Linked ImmunoSorbent Assays (ELISAs) and other assays utilizing antibodies or antibody fragments, complement-based reactions, measurement of absorbance of ultraviolet or other frequency of light, assays utilizing specific receptor-ligand interactions, and other assays known in the art. Assays for detecting other pathogen-related molecules include assays for bacterial sugars and lipids (e.g., bacterial lipopolysaccharide (LPS)), and other assays known in the art. A detector for use with such assays may be an optical detector, a pH detector, an electrochemical detector, a temperature sensor, an ion-sensitive electrode, a radiation detector, or other detector.

In embodiments, devices comprising a sonicator, and systems and methods comprising or using such devices, may comprise a controller. In embodiments, a controller may comprise a processor. In embodiments, a controller may be connected to, and may control the operation of, components of a device; such components are typically disposed within a housing of the device. In embodiments, a controller may control the operation of a sonicator. In embodiments, a controller may control the operation of a sample handling system. In embodiments, a controller may control the operation of a detector. In embodiments, a controller may control the operation of any component or unit of the device. Other components may include, for example, a camera, a chemistry assay unit, a nucleic acid assay unit, a heating unit, a communication unit, a protein chemistry unit, or other component or unit. In embodiments, a controller may control the operation of one or more components of a device according to a protocol. In embodiments, a protocol by which a controller controls the operation of any one or more component or unit of a device may be preprogrammed, e.g., may be resident on the device. In embodiments, a protocol by which a controller controls the operation of any one or more component or unit of a device may be obtained from another device, or from a user, or from a laboratory, or from a network, or from the cloud. In embodiments, a protocol by which a controller controls the operation of any one or more component or unit of a device may be updated, or may be updatable, according to information or instructions from another device, or from a user, or from a laboratory, or from a network, or from the cloud. In embodiments, a device may receive information, or instructions, or updates, or protocols, via a user interface. In embodiments, a device may receive information, or instructions, or updates, or protocols, via a communication assembly.

In embodiments, devices comprising a sonicator, and systems and methods comprising or using such devices, may comprise a display effective to provide a user with information regarding the operation of the device, information regarding the progress of an assay performed by the device, or information regarding the results of an assay performed by the device. In embodiments, a display may comprise a visual display, or may comprise a printed display, or may comprise an audio signal, which may include an audio signal understandable as speech by a user, or may comprise any combination or all of such displays. In embodiments, a display may comprise a user interface. In embodiments in which a display comprises a user interface, a device may receive, e.g., information, commands, protocols, or other input.

In embodiments, devices comprising a sonicator, and systems and methods comprising or using such devices, may comprise a communication assembly effective to communicate with one or more of a user, another device, a laboratory, a network, the cloud, or other communication target. In embodiments, a communication assembly may provide a communication target with information regarding the operation of the device, information regarding the progress of an assay performed by the device, or information regarding the results of an assay performed by the device. In embodiments, a communication assembly may be configured to allow a device to receive, e.g., information, commands, protocols, or other input from an outside source, such as, e.g., a user, another device, a laboratory, a network, the cloud, or other communication source.

DEFINITIONS

Before the present devices, systems, and methods are disclosed and described, it is to be understood that the terminology used herein is for the purpose of describing particular embodiments only and is not intended to be limiting. It is also to be understood that the present disclosure provides explanatory and exemplary descriptions and examples, so that, unless otherwise indicated, the devices, systems, and methods disclosed herein are not limited to the specific embodiments described herein.

It must be noted that, as used in the specification and the appended claims, the singular forms "a," "an" and "the" include plural referents unless the context clearly dictates otherwise. Thus, for example, reference to "a salt" refers to a single salt or mixtures of different salts, and the like.

In this specification and in the claims that follow, reference will be made to a number of terms, which shall be defined to have the following meanings:

Acronyms and abbreviations, such as "rpm" (revolutions per minute), "min" (minute), "sec" (second), and so forth, have their customary meanings.

As sued herein, the term "assay" and grammatical equivalents refers to tests, measurements, observations, and other experimental procedures which may be applied to a sample for detection of an analyte, identification of an analyte, and measurement of the amounts of an analyte in a sample. Assays may be physical assays which detect, identify, or measure a physical property of a sample; assays may be chemical assays, which detect, identify, or measure a chemical property of a sample, or perform chemical reactions in or with a sample; and include assays which use optical, electrical or electronic, chemical, or other means of detection and measurement.

As used herein the term "ultrasound" refers to vibrations at frequencies beyond those capable of being detected by a human subject, i.e., frequencies greater than about 20,000 cycles per second (20 kiloHerz (kHz)).

As used herein the term "ultrasonic energy" refers to the energy of vibrations at frequencies beyond those capable of being detected by a human subject, i.e., frequencies greater than about 20,000 cycles per second (20 kHz). A sonicator may be effective to produce and apply ultrasonic energy.

As used herein, the term "sonicator" refers to a device effective to provide ultrasonic energy, e.g., by providing mechanical energy, typically in the form of vibrations, at ultrasonic frequencies. A sonicator may include a driving element which provides high-frequency vibrations; for example, many sonicators utilize piezoelectric materials to produce high-frequency vibrations. Piezoelectric ultrasound generators typically require high voltages (e.g., about 200 volts (V) to about 400 V) to provide the needed alternating current drive to operate such generators.

As sonicator has a tip portion, which includes the distal tip and portions nearby; ultrasonic energy from a sonicator is typically transmitted to a target material by the tip portion. Sonicators often have sonicator horns, often made from stainless steel, for example, configured to direct ultrasonic energy to a tip portion; where a sonicator has a sonicator horn, the tip of the sonicator horn comprises the sonicator tip, and the tip portion of the sonicator horn comprises the sonicator tip portion.

As used herein, the terms "horn" and "sonicator horn" refer to a portion of a sonicator configured to focus ultrasonic energy, or to provide a pathway for the direction of ultrasonic energy, to a destination. A horn may be designed and configured to transfer or transmit ultrasonic energy in an efficient manner, and may, for example, be configured to resonate at particular frequencies which may be tuned or adapted to particular frequencies of choice of a driving element of a sonicator. A horn may have a tip, or tip portion; a horn tip or tip portion may be configured to maximize energy transfer, e.g., by maximizing contact, to a vessel, or wall of a vessel, or to a fluid contained within a vessel.

As used herein, the terms "fill" and "filled" and their grammatical equivalents, e.g., as used in phrases such as "a vessel may be filled with a sample solution" refer to the transfer of any amount, including partial filling and complete filling. These terms as used herein do not require that such filling completely fill a container, but include any lesser amount of filling as well.

As used herein, the terms "detect", "detection", "detecting" and grammatical equivalents refer to a determination that a target analyte, such as a pathogen-identifying material, is present. Detection does not require that a minimum amount of the target analyte be present in the sample, but merely that the analyte be observed to be present, whether directly or indirectly (although in practical terms, a lower limit below which detection is unlikely to occur may exist).

As used herein, the terms "identify", "identification", "identifying", and grammatical equivalents refer to a determination of the identity of a target analyte found in a sample. Such identification, in addition to detection, may be useful where detection may be ambiguous as to the specific identity of a detected analyte; for example, where an influenza virus is detected, it may further be useful to identify the particular strain, or strains, of influenza found in the sample. Thus, identification may provide more detailed and specific information than does detection.

As used herein, the terms "measure", "measurement", "measuring", and grammatical equivalents refer to a determination of the amounts of a target analyte found in a sample. Thus, measurement provides quantitative information which may not be provided by detection or identification, or which may be more precise that information provided by detection or identification.

The term "nucleic acid" refers to nucleotides and nucleosides which make up, for example, deoxyribonucleic acid (DNA) macromolecules and ribonucleic acid (RNA) macromolecules. Nucleic acids may be identified by the base attached to the sugar (e.g., deoxyribose or ribose); nucleic acid sequences may be used to identify an organism from which the nucleic acid sequence was obtained.

The terms "polypeptide" and "protein" may be used interchangeably to refer to molecules comprised of amino acids linked by peptide bonds. Individual amino acids may be termed "residues" of a polypeptide or protein. Unique amino acid sequences of polypeptides may be used to identify the organisms from which the polypeptides were obtained.

The term "antibody" is used in the broadest sense and specifically covers single monoclonal antibodies (including agonist and antagonist antibodies), antibody compositions with polyepitopic specificity, and antibody fragments. Monoclonal antibodies are obtained from a population of substantially homogeneous antibodies, i.e., the individual antibodies comprising the population are identical except for possible naturally-occurring mutations that may be present in minor amounts. For example, monoclonal antibodies may be made by the hybridoma method first described by Kohler et al., Nature, 256:495 (1975), or may be made by recombinant DNA methods (see, e.g., U.S. Pat. No. 4,816,567 to Cabilly et al.).

"Antibody fragment", and all grammatical variants thereof, as used herein is defined as a (1) portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody, and (2) constructs comprising a portion of an intact antibody (as defined by the amino acid sequence of the intact antibody) comprising the antigen binding site or variable region of the intact antibody. Examples of antibody fragments include Fab, Fab', Fab'-SH, F(ab')$_2$, Fd, Fc, Fv, diabodies, and any other "Non-single-chain antigen-binding unit" as described, e.g., in U.S. Pat. No. 7,429,652.

The term "pathogen" as used herein refers to an agent that may cause a disease, such as an infectious disease, in a subject. Pathogens include, for example, Gram-negative bacteria, Gram-positive bacteria, other bacteria, RNA viruses, DNA viruses, prions, yeast, fungi, protozoans, helminths, nematodes, and any other pathogenic agent which may sicken a subject or, if transmitted from a subject who may not suffer disease, could cause disease in a further subject to which the pathogen is transmitted.

As used herein, "pathogen-identifying material" refers to proteins and nucleic acids derived from a pathogen, such as a bacterium, a prion, a virus, a yeast cell, a fungus, a protozoan (also termed "protist"), a helminth, nematode, or other viral, single cellular or multicellular organism which may be found in a biological sample collected from a subject. Pathogen-identifying material may comprise a target nucleic acid. Pathogen-identifying material may comprise a target peptide, or epitope (e.g., a portion of a peptide). The proteins, and the nuclear material of such organisms (whether DNA or RNA), is indicative of the particular type of organism, and may be used to detect the presence of such an organism, and to identify it. Quantitative measurements of pathogen-identifying material provide measurements of the amounts of such organisms in a biological sample, and may be used to determine the severity of an infection, or to track the progress of a disease, and to track the course and success of its treatment.

The term "probe" as used herein refers to a material which is useful to identify a target compound or cell; a probe may be, e.g., a nucleic acid probe, a protein probe, or other probe. A target compound may be produced by, or found in or on, a prion, a virus, a bacterium, a yeast, a fungus, a protozoan, or other pathogen. A probe, as used herein, may comprise RNA or DNA, or analogs of RNA or DNA, effective that the probe may recognize and bind (e.g., hybridize) to a target nucleic acid. A target nucleic acid may be, e.g., a viral, bacterial, yeast, fungal, protozoan, helminth, nematode, or other nucleic acid sequence (which may be a portion of a longer nucleic acid sequence). A probe, as used herein, may comprise a polypeptide or protein, such as an antibody or antibody fragment, which may recognize and bind to a target compound or portion of a compound (e.g., an epitope of a protein that is indicative of a target pathogen).

As used herein, a "marker", a "label", a "label" and a "label moiety" refer to a detectable compound or composition which is conjugated directly or indirectly to the antibody so as to generate a "labeled" antibody. A label or marker provides a detectable signal for at least the time period during which a signal is to be observed. The label or marker may be detectable by itself (e.g. radioisotope labels or fluorescent labels) or, in the case of an enzymatic label, may catalyze chemical alteration of a substrate compound or composition which is detectable.

A marker or label may be linked (non-covalently or covalently) to a nucleic acid probe, an antibody or antibody fragment, or other probe. A label may alter its detectability (e.g., become detectable, or increase, or decrease its detectability) upon contact with its target. A label may detach from its probe upon contact between the probe and its target, and thus may alter its detectability. Such alterations in detectability are useful in assays for detecting, identifying, or measuring analytes in a sample.

A label may be, for example, a dye, an epitope tag, a fluorescent moiety, a luminescent moiety, a chemiluminescent moiety, an enzymatic label, a magnetic label, a paramagnetic label, a contrast agent, a nanoparticle, a radioisotope, biotin, streptavidin, and a quencher. A nanoparticle may be a particle of an element, such as a gold nanoparticle, or of an alloy or compound, such as a quantum dot (a particle of a semiconductor material), or other particle having a size typically in a range between about 1 nm to about 100 nm.

As used herein, the terms "sample" and "biological sample" refer to a blood, urine, sputum, tears, material from a nasal swab, throat swab, cheek swab, or other bodily fluid, excretion, secretion, or tissue obtained from a subject. These terms are inclusive of an entire sample and of a portion of a sample. As used herein, reference to a fluid sample includes reference to a sample and a biological sample. Such samples may include fluids into which material has been deposited, where such material may be obtained from a nasal swab, throat swab, cheek swab, or other sample which may include solid or semi-solid material, whether along with or without natural fluids. Such fluids and samples comprise fluid samples and sample solutions.

As used herein the "sample solution" refers to a fluid sample itself, and to dilutions, mixtures, aliquots, or other solutions which contain at least a portion of a sample.

As used herein the terms "sample handling system", "fluid handling system" and grammatical equivalents refer to systems configured to obtain, transport, and deliver fluids. In embodiments disclosed herein, such systems comprise pipettes, nozzles, pipette tips, mechanical components configured to move a pipette, a nozzle, or a pipette tip to a desired location. Such a desired location is typically within a housing of a device. In embodiments, a pipette tip may be mounted on a nozzle; in embodiments, a pipette tip may be removably mounted on a nozzle, effective that a nozzle may engage and mount a first pipette tip, use the first pipette tip, discard the first pipette tip, and then engage and mount a second pipette tip. Such systems comprise means for aspirating liquid into a pipette tip. Such systems comprise means for dispensing liquid from a pipette tip. In embodiments of such systems, a pipette and nozzle may engage and mount an element other than a pipette tip; for example, in embodiments disclosed herein, a pipette and nozzle may engage and mate with a mating socket of a vessel (see, e.g., FIGS. 10 and 11). In embodiments, a pipette and nozzle mated with a mating socket of a vessel may be used to transport the vessel to a desired location within a device. In embodiments, a pipette and nozzle mated with a mating socket of a vessel may be used to apply force to a vessel (see, e.g., FIG. 11 for a configuration where such application of force may be useful).

The methods disclosed herein can be readily incorporated into and used in device for processing a sample, or a system for processing a sample, which may be an automated assay device, or may be an automated assay system. Such assay devices and assay systems may comprise devices and systems disclosed, for example, in U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or effect a chemical reaction with one or more reagents or other chemical or physical processing, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a biological sample, e.g., of blood, urine, sputum, material obtained from a nasal swab, a throat swab, a cheek swab, or other sample, (e.g., a sample obtained from a fingerstick, or from venipuncture, or an arterial biological sample, e.g., of blood, urine, sputum, material obtained from a nasal swab, a throat swab, a cheek swab, or other sample), a urine sample, a biopsy sample, a tissue slice, stool sample, or other biological sample; a water sample, a soil sample, a food sample, an air sample; or other sample. A biological sample, e.g., of blood, urine, sputum, material obtained from a nasal swab, a throat swab, a cheek swab, or other sample, may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system (also termed herein a sample handling system). A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component.

The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

A fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a biological sample, e.g., of blood, urine, sputum, material obtained from a nasal swab, a throat swab, a cheek swab, or other sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assay on a sample, and to obtain data from the sample. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. For example, a sample processing device may be configured to detect, or to identify, or to measure pathogen-identifying material in a sample. In embodiments, a sample processing device may be configured to perform a plurality of assays on a single sample. In embodiments, a sample processing device may be configured to perform a plurality of assays on a single biological sample, where the biological sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication assembly that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software.

Embodiments of the devices, systems, and methods disclosed herein are discussed in the examples presented below.

EXAMPLES

The following examples disclose devices comprising a sonicator effective to disrupt pathogens in a biological sample.

Example 1

Systems for Disrupting Pathogens Comprising a Sonicator

Embodiments of systems disclosed herein include devices which have a sonicator configured to apply ultrasonic energy to a sample solution. Application of ultrasonic energy to a sample solution containing a pathogen may be effective to disrupt the pathogen and to release pathogen-identifying material into the solution, where it can be detected and the pathogen identified. In embodiments, the amounts of pathogens present in the sample solution may be quantified following application of ultrasonic energy effective to disrupt the pathogen and to release pathogen-identifying material into the solution. A schematic illustration representing elements of an embodiment of a system comprising devices having a sonicator is shown in FIG. 1.

In embodiments, a tip portion of a sonicator of a device of a system as disclosed herein be configured to improve the transfer of ultrasonic energy to a sample solution, or to provide better contact between the sonicator and a vessel containing a sample solution, or both. In embodiments, a sonicator of a device of a system as disclosed herein may have a sonicator horn; such a sonicator horn may have a tip portion, which may be configured to improve the transfer of ultrasonic energy to a sample solution, or to provide better contact between a sonicator and a vessel containing a sample solution, or both. In embodiments of systems disclosed herein, a system may include a vessel configured to hold a sample, and may include a vessel holder configured to hold a vessel. A sample holder may be configured to place a vessel in a proper position for sonication; may be configured to hold a vessel during sonication (in embodiments, such holding may comprise application of force effective to restrain a vessel during sonication, e.g., to reduce loss of energy due to unwanted motion of a vessel, or for improved energy transfer during sonication); or may be configured to retain a vessel in place until further operation is needed following sonication.

As shown in FIG. 1, in embodiments, a device of a system as disclosed herein may comprise a sample handling system configured to place a sample within a vessel, by, for example, delivering at least a portion of a sample to a vessel and depositing the at least a portion into a chamber of the vessel. A sample handling system may also be configured to place a reagent, or other agent or material, within a vessel, by, for example, delivering the reagent, other agent, or material, to a vessel and depositing it into a chamber of the vessel.

As shown in FIG. 1, in embodiments, a device of a system as disclosed herein may comprise a detector for detecting pathogen-identifying material from a sample. A detector may be any detector effective to detect the presence of pathogen-identifying material in a sample. Such detection may be aided by use of a label or other readily detectable agent, which may be used in conjunction with a reagent that specifically binds to, or reacts with, a pathogen-identifying material.

As shown in FIG. 1, in embodiments, a system as disclosed herein may comprise a controller to operate the components of the system. In embodiments, a device of a system as disclosed herein may comprise a controller to operate components of the device. A controller may comprise a processor, or other component, device, or element effective to oversee and control the operation of a device. A controller may further comprise communication components, devices, or elements effective to provide communication with and between the controller and other components and elements of the device or system. Such internal communication linkages are illustrated in FIG. 1 by dotted lines. It will be understood that, in embodiments of the present devices and systems, other communication linkages may also be provided.

In embodiments, a system as disclosed herein may comprise a communication assembly, which may comprise one or more communications link(s). In embodiments, a device of a system as disclosed herein may comprise a communication assembly, which may comprise one or more communications link(s). Such a communication assembly may comprise a display, for receiving instructions and information, and for providing information and data to a user, or to other components or equipment. In embodiments, such a communication assembly may comprise a one-way communication link (e.g., from the device or system to a user, another device, a laboratory, a network, the cloud, or other communication destination; or to the device or system from a user, another device, a laboratory, a network, the cloud, or other communication source) and, in embodiments, may include a two-way (or multiple-way) communication link(s), e.g., between the device or system and a user, another device, a laboratory, a network, the cloud, or other communication targets. Such communication links with communication destinations or sources are indicated by the dotted arrows in the figure.

In embodiments, a device or system as disclosed herein may comprise a power supply to enable the operation of the components. Power connections are illustrated in FIG. 1 by solid lines. It will be understood that, in embodiments of the present devices and systems, other power connections may also be provided.

As disclosed herein, ultrasonic energy may be applied to a sample by direct contact between the sample and a sonicator (e.g., by immersion of a sonicator tip or tip portion in a sample solution). As disclosed herein, ultrasonic energy may be applied indirectly to a sample, by contacting a sonicator tip portion or tip with a material separating the sonicator tip and the sample solution, where the material is in contact both with the sonicator tip portion or tip, and with the sample solution. In embodiments comprising indirect contact, the material separating the sonicator and the solution may comprise a compliant barrier. In embodiments comprising indirect contact, the material separating the sonicator and the solution may comprise a wall of a vessel containing a sample. In any embodiment comprising indirect contact, the material separating the sonicator and the solution is configured to transmit ultrasonic energy from the sonicator tip portion to the sample solution.

Example 2

Sonicators and Vessels

Figure 2:
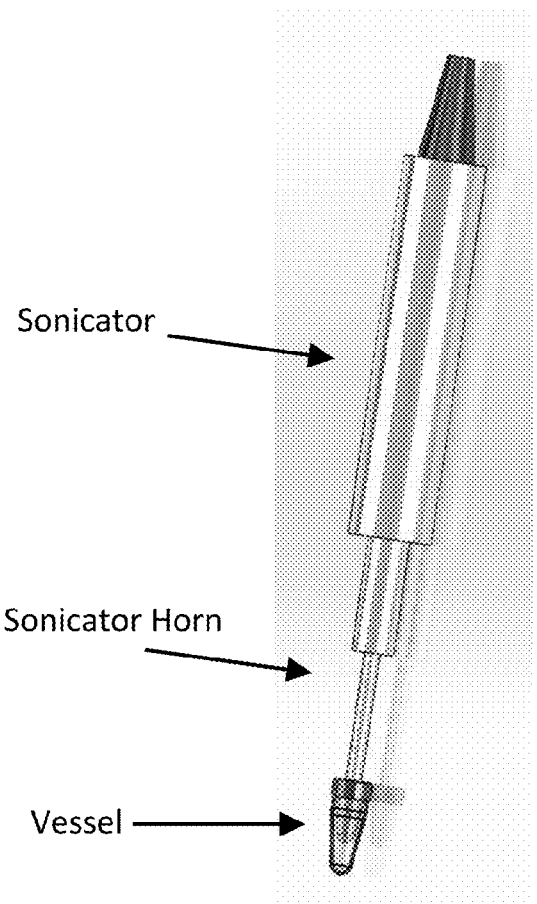
FIG. 2 shows an example of a sonicator suitable for an embodiment of the devices, systems, and methods disclosed herein. In embodiments, a portion of the tip of a sonicator may touch or be inserted into a sample solution in a vessel. In such embodiments, the sonicator tip contacts the sample solution. In an embodiment of configurations illustrated in this figure, the tip portion of the sonicator may be prevented from contacting the sample by the interposition of a compliant barrier material (e.g., the vessel may have a compliant covering, such as a compliant plastic or rubber covering). Pressing the sonicator tip onto a proximal side of the compliant barrier, effective to cause a distal portion of the compliant barrier to contact the solution within the vessel, allows transfer of ultrasonic energy from the sonicator to the sample solution in the vessel while preventing direct contact between the sonicator tip and the sample solution.
Figure 3:
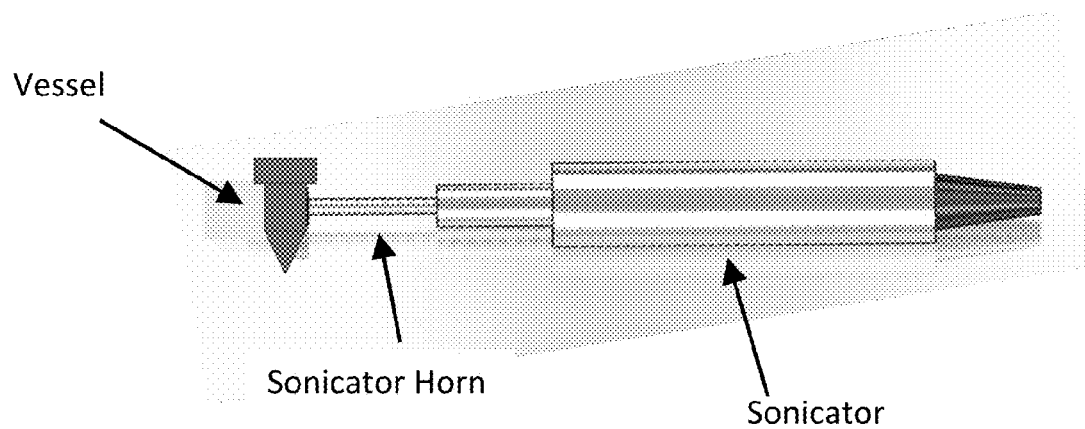
FIG. 3 shows an example of a sonicator suitable for an embodiment of the devices, systems, and methods disclosed herein, in which a portion of the sonicator contacts a wall of the vessel holding a sample solution; in such embodiments, no portion of the sonicator contacts the sample solution, preventing contamination of the sample and of the sonicator, so that there is no requirement to clean or condition the sonicator tip before its re-use.

Examples of sonicators suitable for use in the present devices, systems and methods are shown in FIG. 2 and FIG. 3. FIG. 2 may provide an illustration of an embodiment in which a distal portion of the sonicator (e.g., the tip of the sonicator horn), termed in this example the "tip", contacts a sample solution in a vessel. In such embodiments, the tip contacts the sample solution. Direct contact with the sample solution provides for direct transfer of energy from the sonicator to the sample solution. However, such direct contact requires that the tip touch or enter into the sample solution, providing a possible source of contamination of the sample (and subsequent samples) and requiring cleaning steps and/or coating of the tip to reduce such contamination.

FIG. 2 may also provide an illustration of an embodiment in which the tip is separated from the sample solution by a compliant barrier (such a compliant barrier conforms, to a greater or lesser degree, to the outline of the tip as the tip is pressed into a vessel towards a solution within the vessel). In such an embodiment, the tip contacts the barrier, and the barrier contacts a sample solution in a vessel. In such embodiments, the tip does not contact the sample solution, avoiding possible problems which may arise due to direct contact with the sample solution. Barrier materials tested include latex, nitrile, and polyurethane barriers. However, a compliant barrier may break or become porous during use, and may absorb ultrasonic energy, reducing the efficiency of transferring ultrasonic energy from a tip to a solution.

An alternative embodiment is shown in FIG. 3, which shows an example in which a distal portion of the sonicator contacts a wall of the vessel holding a sample solution; in such embodiments, no portion of the sonicator contacts the sample solution, preventing contamination of the sample and of the sonicator, so that there is no requirement to clean or condition the sonicator tip before its re-use. A wall of a vessel, which may be more rigid, and less compliant than a compliant barrier, may be more efficient at transferring ultrasonic energy from a tip to a solution than a compliant barrier; for example, a rigid wall may absorb less energy than would be absorbed by a compliant barrier.

Although the contact between sonicator and sample solution is indirect in embodiments comprising the configuration illustrated in FIG. 3, ample ultrasonic energy is transferred via the wall of a vessel into a sample solution contained therein, and cells, including pathogen cells, may be, and have been, disrupted in this way. Ultrasonic energy transfer from sonicator to sample solution is improved in this configuration by providing a flat surface on the vessel wall, as disclosed herein, which is complementary to a flat surface on the sonicator tip. Transmission of ultrasonic energy in the configuration illustrated in FIG. 3 is improved by tight contact between a sonicator tip and a wall of a vessel. Application of force between the vessel wall and the sonicator tip is also helpful to provide effective ultrasonic energy transfer from sonicator to sample solution.

Forces of between 1 newton (N) and 16 N have been examined. For example, experiments in which forces of 1, 2, 3, 4, 6, and 10 N were applied to force contact between the tip of a sonicator horn and a polystyrene tube resulted in effective disruption of a test pathogen. In these experiments, 332 µL of solution containing *E. coli* (ATCC 884) bacteria was held in a polystyrene tube. A sonicator probe was applied to the outer wall of the polystyrene tube with 1, 2, 3, 4, 6, and 10 N of force and ultrasonic energy was applied for 10 seconds. Such disruption was comparable to that obtained with a commercial sonicator in which vials are placed in wells in a block connected to an ultrasonic generator. However, the results with 1 N of contact force were variable, and considered inferior to the results obtained with the commercial sonicator. From the results of these and other experiments, it is believed that a contact force of between about 2 N to about 10 N, or between about 2 N to 6 N, or between about 3 N to about 5 N, or about 4 N, is useful for providing effective transfer of ultrasonic energy for disruption of pathogens by contacting a wall of a vessel containing a sample solution.

Different materials exhibit different ultrasonic energy transfer characteristics. For example, preferred vessel materials for ultrasonic energy transfer through a vessel wall include polystyrene, polycarbonate, and polyethylene. Polystyrene was found to be a better material than polycarbonate and polyethylene; polycarbonate was found to be a better material than polyethylene.

Ultrasonic disruption of pathogens may be performed with varying frequencies of ultrasonic energy. Higher frequencies allow for shorter sonicator horns; conversely, sonicators designed to provide ultrasonic energy at lower frequencies will have longer sonicator horns than do sonicators designed for higher frequencies. For example, ultrasonic frequencies suitable for use in devices, systems and methods disclosed herein include ultrasonic frequencies of from about 20 kHz to about 60 kHz, or from about 20 kHz to about 50 kHz, or from about 20 kHz to about 40 kHz. In embodiments of the devices, systems and methods disclosed herein include ultrasonic frequencies devices, systems and methods disclosed herein, suitable ultrasonic frequencies include frequencies of about 20 kHz, about 25 kHz, about 28 kHz, about 30 kHz, about 35 kHz, about 40 kHz, about 45 kHz, about 50 kHz, about 55 kHz, and about 60 kHz.

Figure 4:
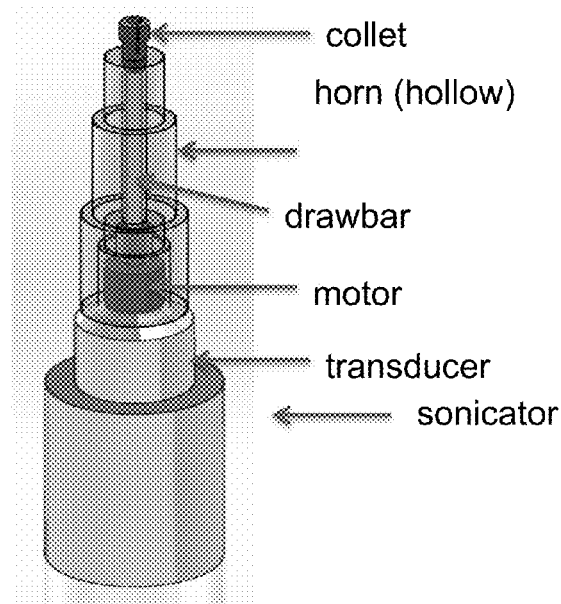
FIG. 4 shows an example of an embodiment of a sonicator having a collet for holding a vessel. The collet may be cinched around a vessel contained within the collet to provide a tight fit between the collet and vessel; such a tight fit may aid in the efficient transfer of ultrasonic energy between the transducer of the sonicator (via the collet) and the vessel.

A sonicator may include or have attached to it multiple elements. FIG. 4 shows an example of an embodiment of a sonicator having a transducer, a motor, a drawbar, and a collet. In embodiments, a motor may be effective to move (e.g., rotate) a drawbar connected to a collet at the tip of the sonicator. As shown in FIG. 4, such a sonicator may have a hollow sonicator horn; in the embodiment shown, the hollow sonicator horn encloses, and allows passage of, a drawbar which provides functional connection between a collet at the distal end of the sonicator and transducer (and thus with the sonicator body as well). A drawbar such as the drawbar shown in the figure that is connected to a collet and a motor may be used to cinch a collet around a vessel contained within the collet to provide a tight fit between the collet and vessel; such a tight fit may aid in the efficient transfer of ultrasonic energy between the transducer of the sonicator (via the collet) and the vessel. As shown in the figure, a sonicator having such a horn and drawbar may be configured to transfer ultrasonic energy from its proximal end (shown here adjacent the motor, near the transducer) to its distal end (adjacent the collet). A collet such as the collet shown in the figure may be configured to mate with and hold a vessel effective to provide ultrasonic energy to a sample within a vessel. In embodiments, a sonicator having such components at its tip may be configured to transfer ultrasonic energy to a sample solution, and in embodiments, may be configured to transfer ultrasonic energy to a sample solution via a vessel wall.

Figure 5:
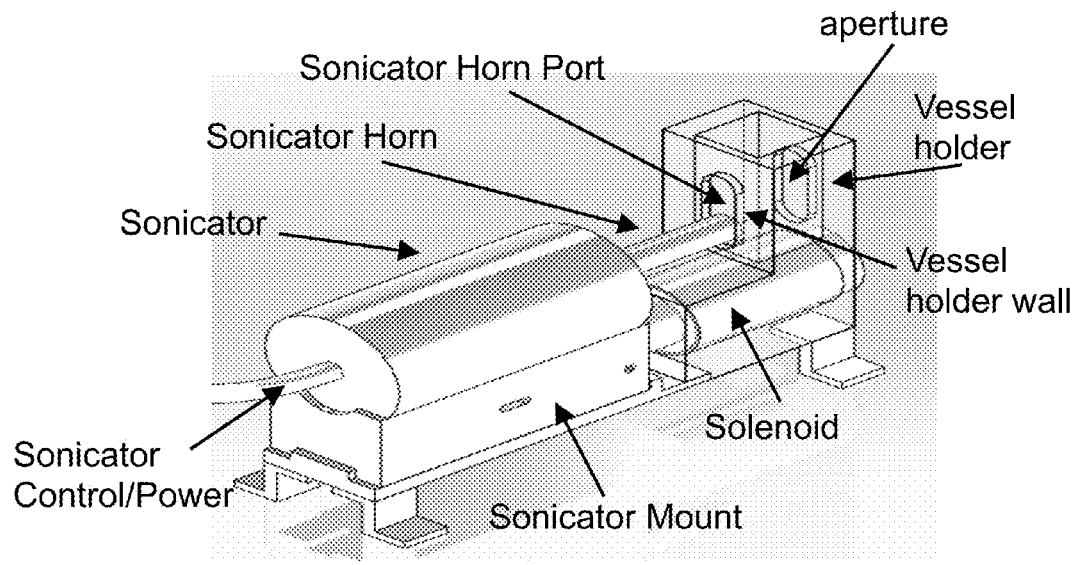
FIG. 5 shows an example of a sonicator mounted for use in an embodiment of the devices disclosed herein. As shown, a distal portion of the sonicator passes through a port in a vessel holder, allowing direct contact between the sonicator and a wall of a vessel held by the vessel holder. As shown, a vessel holder may have a further aperture, allowing access to another portion of the vessel, and including optical access without requiring an optical path through a wall of the vessel holder. As shown, a vessel holder may have walls without apertures; such walls may be configured for optical access as well, by construction using suitable materials; by providing a wall of proper flatness, orientation, or thickness of the wall; by proper preparation or construction of the wall surface, or by other means.

As shown in FIG. 5, a sonicator may be mounted on a movable mount for use in an embodiment of the devices disclosed herein. The sonicator mount shown in FIG. 5 is operably connected to a solenoid, effective that when the solenoid is activated, the sonicator mount, and its attached sonicator, are drawn towards the solenoid (in a distal direction with reference to the sonicator). This motion moves the sonicator horn in the same (distal) direction, moving the tip of the sonicator horn deeper into the sonicator horn port of the vessel holder. When a vessel is in place within the vessel holder, activation of the solenoid and the resulting movement presses the tip of the sonicator horn into contact with a side wall of the vessel. In embodiments, the action of the solenoid generates a force at the area of contact between the tip of the sonicator horn and the vessel wall. Such a force may be, for example, between about 2 N and about 10 N, or between about 2 N and about 6 N, or preferably between about 3 N and about 5 N, or, in embodiments, about 4 N of force.

As shown, a vessel holder may have a further aperture, allowing access to another portion of the vessel, and including optical access without possible interference by the vessel holder. As shown, a vessel holder may have walls without apertures; such walls may be configured for optical access as well, by construction using suitable materials; by providing a wall of proper flatness, orientation, or thickness of the wall; by proper preparation or construction of the wall surface, or by other means.

Figure 6A:
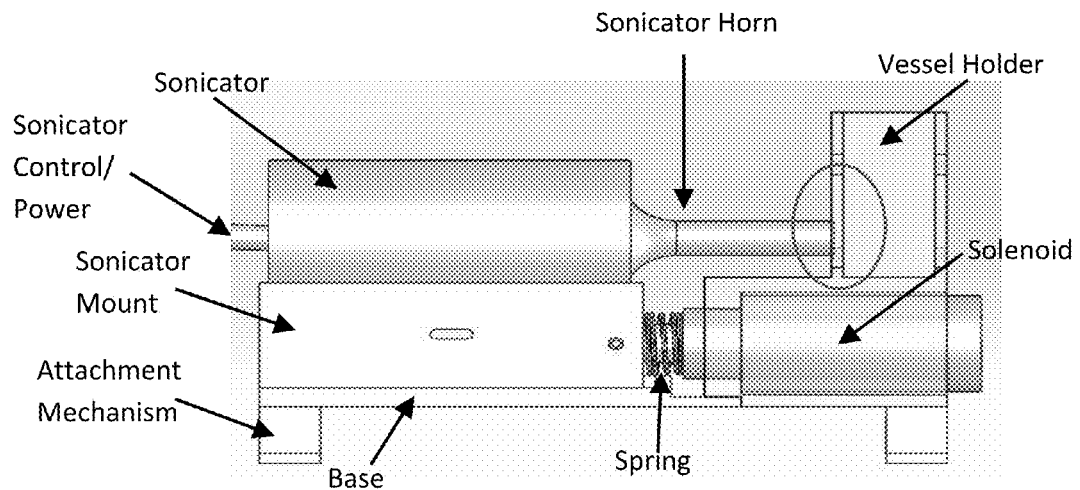
FIGS. 6A and 6B provide views of an embodiment of a sonicator and sonicator assembly suitable for devices, systems, and methods as disclosed herein.
Figure 6B:
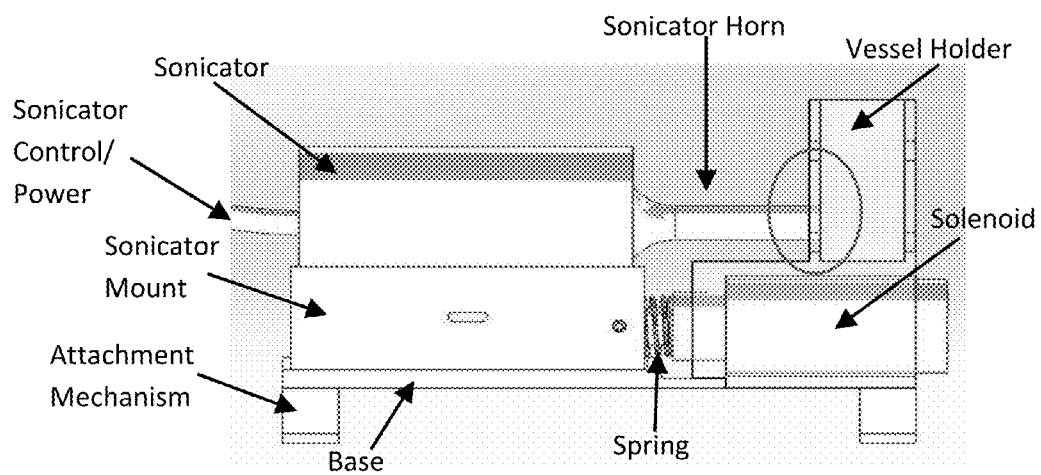

FIG. 6 provides further illustration of the design and operation of a movable sonicator operably connected to a solenoid for moving a sonicator horn tip into functional contact with a wall of a vessel containing a sample solution. FIGS. 6A and 6B present a side view of an embodiment of a sonicator mounted and operably connected with a solenoid that is configured to move the sonicator horn in a transverse direction. In FIG. 6A, the solenoid is not activated. FIG. 6A shows a side view of an embodiment of a sonicator mounted with a solenoid configured to move the sonicator horn in a transverse direction (e.g., leftwardly or rightwardly as shown in the figure). The oval encloses an area of interest, in which the sonicator horn tip moves to and contacts a vessel wall when a vessel is in place within the vessel holder. As shown, a spring is provided to urge the sonicator away from the vessel holder upon release of solenoid force drawing the sonicator towards the vessel holder. The sonicator horn is disposed so as to approach a vessel held within the vessel holder when the sonicator is moved to the right in the figure. At rest (with the solenoid off), as shown in FIG. 6A, the sonicator horn does not contact a vessel held within the vessel holder, and the spring is in an extended conformation.

The solenoid is activated in FIG. 6B, the sonicator horn is in contact with an outer wall of a vessel held within the vessel holder, and the spring is in a compressed conformation. Operation of the sonicator in this configuration, in which the sonicator horn is in contact with a wall of a vessel held within the vessel holder, is effective to provide ultrasonic energy to a sample solution within the vessel. Transfer of ultrasonic energy is improved by providing a firm contact between the sonicator horn tip and the vessel wall; as discussed above, ultrasonic energy transfer is improved by providing transverse force (towards the vessel wall) of between about 2 N and about 10 N, or between about 2 N and about 6 N, or about 3N to about 5N, or about 4 N of force. Providing sufficient ultrasonic energy for a sufficient amount of time is effective to disrupt cells within the sample solution; in particular, pathogen cells within the sample solution may be disrupted, effective to release pathogen-identifying material for detection, identification, and measurement.

Figure 7:
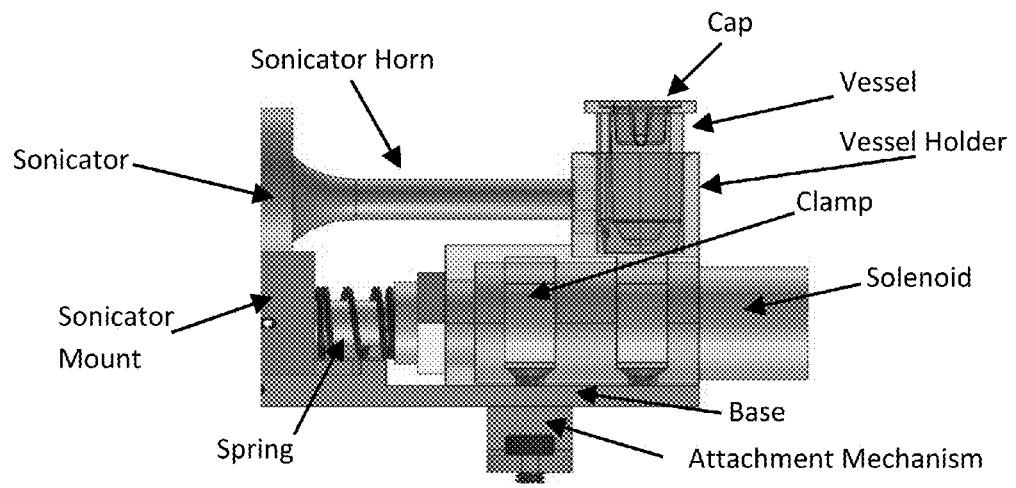
FIG. 7 provides a further example of a solenoid assembly suitable for use in the devices and systems disclosed herein. In this figure, the vessel is covered with a cap; such a cap is effective to prevent loss of sample fluid during sonication, and to prevent spread of sample contents (by spillage, aerosolization, or other means) outside the vessel. In this figure, a vessel is shown held in a vessel holder, and a sonicator horn is shown in contact with a side wall of the vessel. Such a configuration is an operative configuration effective to disrupt cells within the sample solution, such as pathogen cells within the sample solution.

FIG. 7 provides a further, more detailed illustration of contact between sonicator horn tip and a vessel wall. The vessel is held in the vessel holder; in this example, the vessel has a vessel cap. In embodiments, a vessel may be filled with a sample solution prior to placement of the vessel cap. In embodiments, a vessel may be filled with sample solution through a vessel cap, e.g., by a conduit through the vessel cap. Such a conduit may be temporary (e.g., may be provided by a hollow needle piercing the cap, where the path of the needle may reseal following removal of the needle from the cap). Such a conduit may be permanent, e.g., may be a channel or tube that is a permanent feature of the vessel cap. In embodiments, such a conduit may itself be capped. In embodiments, the vessel may be filled by the sample handling system. In embodiments, the cap may be placed on the vessel by the sample handling system following filling of the vessel. In embodiments, the cap may be removed by the sample handling system; for example, in embodiments, the cap may be removed by the sample handling system prior to filling the vessel with sample solution.

A cap as shown in FIG. 7 may be effective to prevent loss of sample fluid during sonication, and to prevent spread of sample contents (by spillage, aerosolization, or other means) outside the vessel. In this figure, a vessel is shown held in a vessel holder, and a sonicator horn is shown in contact with a side wall of the vessel. Such a configuration is an operative configuration effective to disrupt cells within the sample solution, such as pathogen cells within the sample solution.

Figure 8:
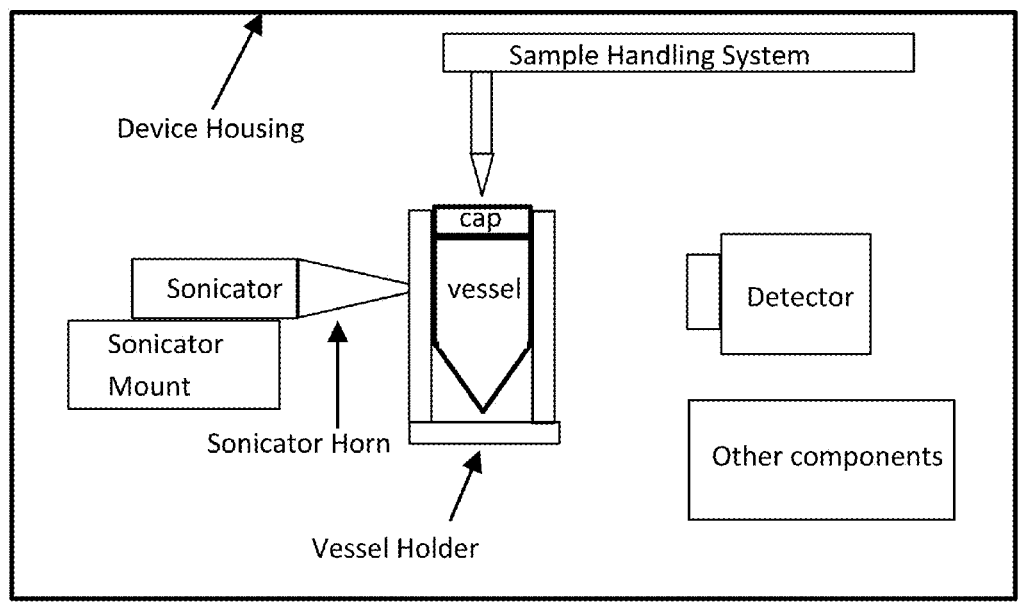
FIG. 8 provides a schematic illustration of a device having a sonicator and other features as disclosed herein. The device illustrated by the figure has a sonicator with a sonicator horn, which can be made to contact a wall of a vessel (e.g., by motion of a movable sonicator mount, as indicated in the figure). The vessel can contain a sample solution, and is configured to be held by a vessel holder. As shown, a vessel cap may be disposed on a surface of the vessel. A sample handling system may be provided effective to transport a biological sample, or a portion thereof, and reagents if applicable, to the vessel. As discussed herein, a sample handling system may also be configured to manipulate or move a vessel, a vessel cap, or other article, within a housing of a device. A device may have a detector, e.g., within the device housing as illustrated in the figure, such as a detector configured to detect pathogen-identifying materials released by sonication of a sample solution. A device may further include other components for performing assays, detecting analytes, and collecting and communicating data obtained from biological samples.

A schematic illustration of a device having a sonicator and other features as disclosed herein is provided in FIG. 8. The device illustrated by the figure has a sonicator with a sonicator horn, which can be made to contact a wall of a vessel (e.g., by motion of a movable sonicator mount, as indicated in FIGS. 6A, 6B, and 7). The vessel can contain a sample solution, and is configured to be held by a vessel holder. The vessel shown in FIG. 8 has a vessel cap. A sample handling system may be provided effective to transport a biological sample, or a portion thereof, and reagents if applicable, to the vessel. As discussed herein, a sample handling system may also be configured to manipulate or move a vessel, a vessel cap, or other article, within a housing of a device. A device may have a detector, e.g., within the device housing as illustrated in the figure, such as a detector configured to detect pathogen-identifying materials released by sonication of a sample solution. A device may further include other components for performing assays, detecting analytes, and collecting and communicating data obtained from biological samples, and other actions. Such components may include, e.g., components configured to perform assays, or to mix reagents, cameras, light sources, lenses, filters, temperature control devices; temperature, optical, chemical or electronic sensors; mechanical components associated with such components, within the device housing as illustrated in the figure.

A sonicator may be used to deliver ultrasonic energy to a sample. In embodiments, a sonicator may be used to deliver ultrasonic energy to a sample in a vessel by contacting a vessel wall, and applying ultrasonic energy to the wall effective to transfer ultrasonic energy to the sample within the vessel. The amount of energy provided by a sonicator may depend on the ultrasonic frequency of the ultrasonic energy applied. The amount of energy provided by a sonicator may depend on the amplitude of the ultrasonic energy. The amount of energy provided by a sonicator may depend on the duration of the application of the ultrasonic energy. The amount of energy provided by a sonicator may depend on the duty cycle of the application of ultrasonic energy (e.g., where the ultrasonic energy is not applied continuously for a duration, but is applied for a first time period, application of ultrasonic energy is ceased for rest time period, and then ultrasonic energy is applied for a second time period, the combination of such periods may be termed a "duty cycle"; a duty cycle may be repeated to provide multiple periods during which ultrasonic energy is applied, separated by rest periods). The amount of energy provided by a sonicator may depend on the shape of the time-varying ultrasonic energy applied (e.g., ultrasonic energy may be produced by a transducer driven by square wave, sawtooth wave, sine wave, or other shaped signals).

In embodiments, a sonicator may be used to disrupt a cell, such as a pathogen cell in a sample. In embodiments, a sonicator may be used to mix a solution; for emulsification of a solution or a mixture of solutions; for resuspension of a material, e.g., resuspension of a sample following centrifugation of the sample; for aerosolization of a liquid; to heat a solution; to disperse a sample in, or into, a solution; to disintegrate a material; to de-gas a liquid; and for other uses. The power requirements for one use of a sonicator may differ from the power requirements of another use of a sonicator. For example, the power required to disrupt a cell in a solution may be greater than the power required to mix a solution. The duration of power applied to a solution may differ depending on the use of the sonicator; for example, the duration of application of ultrasonic power used to heat a solution will depend on the initial temperature of the solution, and the desired final temperature. The shape of the control signal sent to an ultrasonic transducer affects the power applied to a solution, and some shapes may be more effective than others depending on the use of the sonicator.

Figure 9:
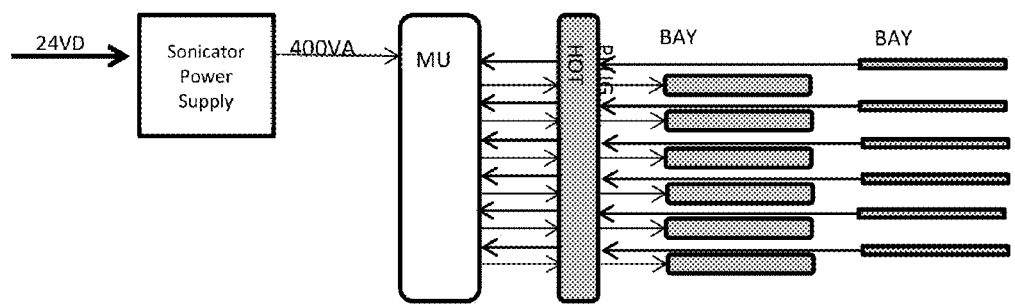
FIG. 9 provides a schematic diagram of an embodiment of a portion of a device having multiple, multiplexed sonicators. In a device comprising multiple sonicators, such sonicators and the associated multiplexer, power supply, cabling, controller, and other associated components are typically placed within the housing of a device. In a system comprising multiple sonicators, which may not all be in the same device, such sonicators and the associated multiplexer, power supply, cabling, controller, and other associated components are typically placed within separate housings, e.g., within the housings of the corresponding devices of the system.

A device as disclosed herein may comprise more than one sonicator. A system as disclosed herein may comprise more than one sonicator. In an embodiment as shown in FIG. 9, a single power supply may provide power to drive multiple sonicators, where the power supply is connected via a multiplexer to the sonicators. In the example shown in FIG. 9, a single 24 volt, 2 Amp (DC) power supply can output about 200 V to about 400 V (AC, at 40 Khz) via a single 6 channel probe power multiplexer effective to distribute six multiplexed output lines to six sonicators. In embodiments, such a configuration may provide six devices, in a system comprising multiple devices (e.g., where each device may be termed a "bay" as indicated in FIG. 9). In embodiments, the output lines may be detachable lines, configured to disengage a bay when desired or needed, and configured to allow reconnection to the power supply when desired or needed (such connections may be termed "hot plugs" as indicated in the figure) . A multiplexer may be configured to control the sonicator pulse duration, or amplitude, or both, and so to control the duration of ultrasonic power transfer to a sample solution. The operation of the multiplexer selection may be according to a set pattern or frequency, or may be controlled, for example, by a controller as shown in FIG. 1, or may be controlled by other means. In embodiments of devices and systems disclosed herein, 2, 3, 4, 5, 6, 7, 8, 9, 10, or more sonicators may be configured in this way, and may be controlled in this way.

In embodiments, a single sonicator may contact a plurality of vessels. In embodiments in which a single sonicator contacts a plurality of vessels, the vessels may be disposed in an array of vessels. An array of vessels may be a linear array, in which a sonicator may move along the array and contact vessels sequentially. An array of vessels may be circular, or semicircular array, in which a sonicator rotates around an axis effective to position the sonicator tip for contact with vessels disposed in such a circular or semicircular array. An array of vessels may comprise a combination of linear and curved arrays, may have an irregular shape, or vessels may be disposed in any shaped array suitable for contact with a sonicator tip.

In embodiments, multiple sonicators may contact a plurality of vessels, e.g., with a first sonicator contacting a first vessel, a second sonicator contacting a second vessel, and so forth. In embodiments in which multiple sonicators contact a plurality of vessels, the vessels may be disposed in an array of vessels. In embodiments in which multiple sonicators contact a plurality of vessels, the sonicators may be disposed in an array of sonicators. An array of sonicators, an array of vessels, and both arrays, may be a linear array, may be a curved array, may be a combination of such arrays, may be an irregular array, and may be any shaped array suitable for contact between a sonicator tip and a vessel.

Figure 10:
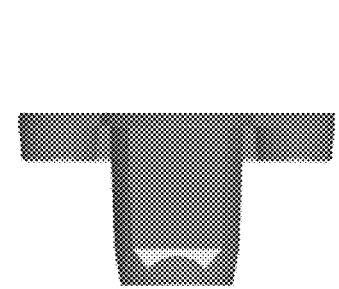
FIGS. 10A-10D provide examples of embodiments of vessels suitable for containing a sample solution for sonication.
Figure 10:
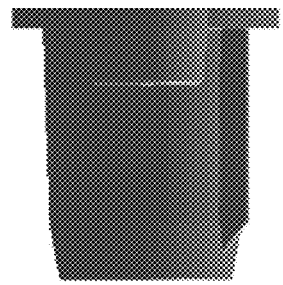
Figure 10C:
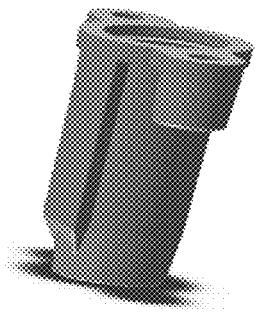
Figure 10D:
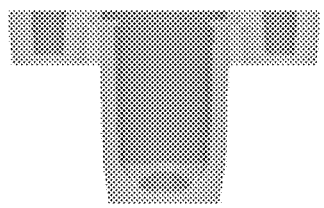

An embodiment of a vessel suitable for containing a sample solution for sonication is shown in several views in FIG. 10. A side view of a vessel, with a flat wall surface facing outward, and the opening (for filling the vessel) shown at the top is provided in FIG. 10A. A side view with a flat wall surface facing rightward is shown in FIG. 10B while FIG. 10C shows an angled view of the vessel. FIG. 10D shows a cross-sectional view of a vessel. The vessel of this embodiment has a flat side wall and a flat bottom; both the flat side wall and the flat bottom are configured to make effective contact with a tip portion of a sonicator, such as a tip of a sonicator horn to provide for transfer of ultrasonic energy from the sonicator to a sample solution within the vessel. The wider portion at the top of the vessel includes surfaces and mating sockets. The mating sockets comprise recesses configured for engagement of a transport and/or force-providing member (e.g., a nozzle of a sample handling system) which a) allows transport of the vessel and b) provides a surface for provision of downward force to oppose upward force of a sonicator horn placed on a flat bottom surface of the vessel. Openings of the mating sockets are visible in this view, as is an inner ridge within the internal chamber of the vessel. In embodiments, mating sockets may be configured to mate with a mechanical component configured to transport a vessel, or to apply force to a vessel, or both. In embodiments, such a mechanical component may be, or may comprise, a sample handling system. In embodiments, such a mechanical component may comprise a pipette, a nozzle, or other mechanical component.

FIG. 11 provides further embodiments of vessels suitable for containing a sample solution for sonication. Embodiments of vessels shown in FIG. 11 have rounded bottoms, which are believed to be more suitable for mixing, re-suspension, and other applications in which a sonicator is applied to a wall of a vessel. FIGS. 11A, 11C, and 11D show embodiments of tubular vessel with rounded bottoms. FIG. 11B shows an embodiment of a conical vessel with a rounded bottom. FIG. 11C an embodiment of an elongated tubular vessel with a rounded bottom. FIG. 11D shows an embodiment of a wide tubular vessel with a rounded bottom. The vessels shown in FIG. 11 are shown with caps; it will be understood that a vessel may not be provided with a cap. In embodiments, caps may be removable. In embodiments, caps may not be removable, but may be piercable effective to fill a vessel without removing the cap. In embodiments, caps may not be removable, but may comprise a passage for filling or dispensing.

FIG. 12 provides yet further embodiments of vessels suitable for containing a sample solution for sonication. FIG.

12A shows an embodiment of a tubular vessel with a rounded bottom and a tapered (e.g., partially conical-shaped cap). A cap as shown in FIG. 12A may form a tight seal with the lip of the vessel when pressed downwardly, due to its partially conical shape. A cap as shown in FIG. 12A may protrude into the interior of the vessel, or in embodiments, may protrude into the vessel only a small amount, or in embodiments, may not protrude into the vessel. FIG. 12B shows an embodiment of a conical vessel with a rounded bottom having flat side surfaces configured to engage with a sonicator tip. As indicated by the example of the embodiments of FIG. 11B and FIG. 12 B, a conical vessel may have one, two, three or more flat surfaces configured for contact with a sonicator. In embodiments, a conical vessel may have no such flat surfaces, but a sonicator tip may press against the outer wall of a conical vessel lacking such surfaces as indicated in FIG. 11B and FIG. 12B. FIG. 12C shows an embodiment of an elongated tubular vessel with a rounded bottom and a protruding flat surface configured to engage with a sonicator tip. It will be understood that, in embodiments, an elongated tubular vessel with a rounded bottom may have two. Three, or more protruding flat surface configured to engage with a sonicator tip. FIG. 12D shows an embodiment of a wide tubular vessel with a rounded bottom having a cap connected to the vessel via cap linkage. Such a cap may be removable, yet remain linked to the remainder of the vessel. A cap linkage may comprise a hinge, a tab, a thread, a perforated tab, or any element effective to connect the cap with the vessel body and allow the opening and closing of the vessel by movement of the cap.

Figure 13:
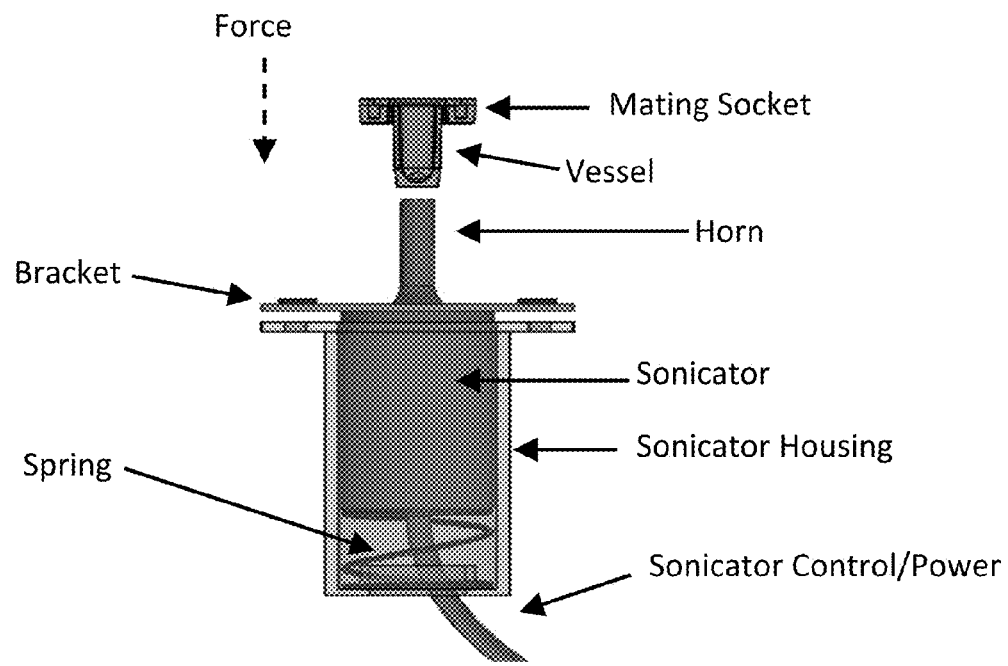
FIG. 13 illustrates a configuration in which a vessel having a flat bottom is disposed to contact a tip of a sonicator. Such contact is effective to transfer ultrasonic energy to the wall of the vessel and thereby to a sample solution contained within the vessel, effective to disrupt cells in the sample solution when the sonicator is activated. Functional contact between the vessel and the sonicator may be aided or improved by the spring shown in the figure. (Note that the action and function of the spring in this figure is opposite to that of the springs shown in FIGS. 6A, 6B, and 7. The present spring acts to urge the sonicator and vessel together; the springs shown in FIGS. 6A, 6B, and 7 act to urge the sonicator and vessel apart from each other.) Functional contact between the vessel and the sonicator may be aided or improved by application of force (as illustrated by the downward arrow in the figure) urging the vessel onto the tip of the sonicator horn, improving functional contact and improving energy transfer from the sonicator to the sample solution and cells within it.

As shown in FIG. 13, a vessel having a flat bottom may be contacted as illustrated by a tip of a sonicator. Such contact is effective to transfer ultrasonic energy to the wall of the vessel and thereby to a sample solution contained within the vessel, effective to disrupt cells in the sample solution. In embodiments, a sonicator tip may contact a wall of a vessel, such as a lower wall as illustrated in FIG. 13, while the vessel is held in a vessel holder. In embodiments, a vessel held in a vessel holder may be in contact with no other components that provide restraint or retaining forces. For example, in embodiments, a sonicator tip may contact a wall of a vessel, such as a lower wall as illustrated in FIG. 13, while the vessel is held in a vessel holder without contact of a nozzle with a mating socket.

In embodiments, functional contact between the vessel and the sonicator may be aided or improved by application of force (as illustrated by the downward arrow in the figure) urging the vessel onto the tip of the sonicator horn, improving functional contact and improving energy transfer from the sonicator to the sample solution and cells within it. Force urging contact between the sonicator tip and the vessel bottom may be provided by a spring, e.g., a spring as shown in the figure. In embodiments, a nozzle of a sample handling system, or two nozzles of a sample handling system, may engage with one or both mating sockets, and apply downward force effective to urge the base of the vessel onto the sonicator tip to improve contact between the vessel and the sonicator tip. In further embodiments, where one or two nozzles of a sample handling system engage with one or both mating sockets, and apply downward force effective to urge the base of the vessel onto the sonicator tip, such application of force in conjunction with the presence of the spring shown in FIG. 13 may improve the contact, or improve control of the amount or effect of the applied force. The action and function of the spring shown in FIG. 13 is to urge the sonicator and vessel together. This action is opposite to that of the springs shown in FIGS. 6A, 6B, and 7, which act to urge the sonicator and vessel apart from each other.

Thus, in embodiments, force urging contact between a sonicator tip and a vessel wall may be provided by one or more of a solenoid, a spring, a sample handling system, or other means.

Sonication is effective to disrupt cell membranes. Sonication may be used to release pathogen-identifying material into a sample solution effective to assay the sample, to detect the presence of pathogens, to identify pathogens present in the solution, and to measure the amount of pathogens present in the solution. Pathogens tested using devices with sonicators as disclosed herein included $E.$ $coli$ 884, $S.$ $pneumonia$ 3508, and Adenovirus 1.

Figure 14:
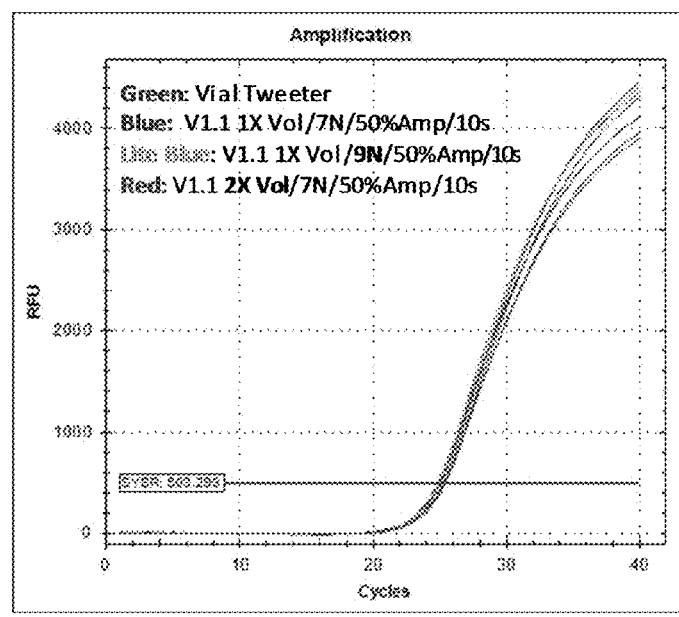
FIG. 14 presents the results of quantitative polymerase chain reaction (qPCR) measurements made from pathogen-identifying material released for assay by sonication according to the present methods. The horizontal axis represents the number of cycles while the vertical axis (in relative light units) represents the numbers of copies of the target nucleic acid sequence indicative of the target pathogen. As shown in the figure, all target nucleic acids were detectable after about 25 cycles.

Since nucleic acids are enclosed by cell or viral membranes, detection of target pathogens demonstrates that the sonication has disrupted these membranes and made the pathogen-identifying nucleic acids available for assay. As shown in FIG. 14, pathogens were detected following sonication using quantitative polymerase chain reaction (qPCR). qPCR assays detect target nucleic acids indicative of the target pathogen; repeated cycles double the number of copies of the target (if present); this process is termed amplification. Other detection methods may also be used, including other PCR methods known in the art, other nucleic acid assays known in the art, ELISA assays, other antibody-based assays, hemagglutinin assays (e.g., for influenza), and other assays. The horizontal axis of FIG. 14 represents the number of cycles while the vertical axis (in relative light units) represents the numbers of copies of the target nucleic acid sequence indicative of the target pathogen. The horizontal line near the bottom of the figure (labeled "SYBR 503.299") indicates the lower limit for detection of pathogen nucleic acids. The cycle number at which a trace passes this threshold is the "cycle threshold" or "Ct" number; a target is considered detected when the results pass the threshold. A control (the traces at the far-right of the figure, labeled "VialTweeter") is shown, in which pathogen-containing solutions in polypropylene containers mounted in wells of a block connected to an ultrasonic generator were subjected to sonication). The other traces result from experiments in which a sonicator tip contacted walls of vessels holding pathogen-containing solutions. As shown in the figure, nucleic acids from target pathogens were detectable after about 25 cycles. Thus, sonication as disclosed herein may be effective to disrupt pathogens for use in the detection, identification, and measurement of pathogens in a sample.

While the above is a complete description of the preferred embodiment as described herein, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

This document contains material subject to copyright protection. The copyright owner (Applicant herein) has no objection to the facsimile reproduction by anyone of the patent document or the patent disclosure, as they appear in the US Patent and Trademark Office patent file or records, but otherwise reserves all copyright rights whatsoever. The following notice shall apply: Copyright 2013 Theranos, Inc.

The invention claimed is:

1. A device configured to assay a sample for the presence of pathogen-identifying material, said device comprising a housing, and within said housing, a sonicator having a sonicator tip; a vessel holder configured to hold a vessel having a vessel wall; a sample handling system configured to move said vessel within the housing, wherein the vessel is configured to hold said sample for sonication; a solenoid disposed to urge said sonicator tip towards the vessel wall when said solenoid is activated, wherein the sonicator tip is configured to contact the vessel wall effective to transfer ultrasonic energy from said sonicator to the vessel wall upon operation of the sonicator; a spring disposed so as to urge the sonicator tip away from the vessel wall; and a detector.

2. The device of claim 1, wherein said sonicator comprises a sonicator horn comprising said sonicator tip, wherein the sonicator tip is configured to contact said vessel wall effective to transfer ultrasonic energy from the sonicator to the vessel wall upon operation of the sonicator.

3. The device of claim 1, wherein said detector comprises an optical detector.

4. The device of claim 1, further comprising a communication assembly configured to communicate with a laboratory, a network, or the cloud.

5. The device of claim 1, wherein the device is configured to apply force to said vessel while applying said sonicator tip to said vessel wall of the vessel.

6. A device configured to assay a sample for the presence of pathogen-identifying material, said device comprising a housing; a sonicator within said housing, said sonicator having a sonicator tip; a sample handling means configured to move a vessel within the housing; a vessel holding means configured to hold said vessel, the vessel having a vessel wall and being configured to hold said sample for sonication; a solenoid disposed to urge said sonicator tip towards said vessel wall when said solenoid is activated, wherein the sonicator tip is configured to contact the vessel wall effective to transfer ultrasonic energy from said sonicator to the vessel wall upon operation of the sonicator; a spring disposed so as to urge the sonicator away from the vessel wall; and a detector means.

7. The device of claim 6, wherein said sonicator tip is configured to contact said vessel wall effective to transfer ultrasonic energy from the sonicator to the vessel wall upon operation of the sonicator.

8. The device of claim 6, wherein said detector means comprises optical detection means.

9. The device of claim 1, wherein said assay for the presence of the pathogen-identifying material comprises an assay selected from the group consisting of detection of the pathogen-identifying material in the sample, identification of the pathogen-identifying material in the sample, and measurement of an amount of the pathogen-identifying material in the sample.

10. The device of claim 6, wherein said assay for the presence of the pathogen-identifying material comprises an assay selected from the group consisting of detection of the pathogen-identifying material in the sample, identification of the pathogen-identifying material in the sample, and measurement of an amount of the pathogen-identifying material in the sample.

11. The device of claim 1, wherein said biological sample comprises a sample selected from the group consisting of blood, urine, sputum, tears, material from a nasal swab, material from a throat swab, material from a cheek swab, and another bodily fluid, excretion, secretion, and tissue obtained from a subject.

12. A system comprising the device of claim 1.

13. The device of claim 1, wherein said sample handling system is configured to apply force to the vessel while the sonicator tip is applied to the vessel wall of the vessel.

* * * * *